United States Patent [19]
Lee et al.

[11] Patent Number: 5,827,733
[45] Date of Patent: Oct. 27, 1998

[54] GROWTH DIFFERENTIATION FACTOR-8 (GDF-8) AND POLYNUCLEOTIDES ENCODING SAME

[75] Inventors: Se-Jin Lee; Alexandra C. McPherron, both of Baltimore, Md.

[73] Assignee: The Johns Hopkins University School of Medicine, Baltimore, Md.

[21] Appl. No.: 525,596

[22] PCT Filed: Mar. 18, 1994

[86] PCT No.: PCT/US94/03019

§ 371 Date: Oct. 26, 1995

§ 102(e) Date: Oct. 26, 1995

[87] PCT Pub. No.: WO94/21681

PCT Pub. Date: Sep. 29, 1994

Related U.S. Application Data

[63] Continuation-in-part of Ser. No. 33,923, Mar. 19, 1993, abandoned.

[51] Int. Cl.⁶ .......................... C07K 14/475; C12N 1/21; C12N 5/10; C12N 15/12

[52] U.S. Cl. .................. 435/325; 435/69.1; 435/69.4; 435/320.1; 435/172.3; 435/252.3; 530/350; 530/397; 530/399; 536/23.1; 536/23.5; 536/23.51; 536/24.33

[58] Field of Search ..................................... 530/350, 397, 530/399; 435/69.1, 69.4, 320.1, 172.3, 240.1, 252.3, 325; 536/23.1, 23.5, 23.51, 24.33

[56] References Cited

PUBLICATIONS

Bowie et al. Science 247:1307–1310, 1990.
Rudinger. Peptide Hormones, Parsons, ed., University Park Press, Baltimore, pp. 1–7, 1976.
Wells. Biochemistry 29:8507–17, 1990.
Ngo et al. The Protein Folding Problem and Tertiary Structure Prediction. Merz et al., eds., Birkhauser, Boston, pp. 491–495, 1994.
Massague. Cell 49:437–438, 1987.
Callard et al. The Cytokine FactsBook, Academic Press, London, pp. 31–32, 1994.

*Primary Examiner*—Elizabeth C. Kemmerer
*Attorney, Agent, or Firm*—Fish & Richardson, P.C.

[57] ABSTRACT

Growth differentiation factor-8 (GDF-8) polypeptides, polynucleotides encoding GDF-8 polypeptides, and vectors and host cells containing GDF-8 encoding polynucleotides are provided.

11 Claims, 15 Drawing Sheets

```
  1 TTAAGGTAGGAAGGATTTCAGGCTCTATTTACATAATTGTTCTTTCCTTTTCACACAGAA  60
                                                              N
 61 TCCCTTTTTAGAAGTCAAGGTGACAGACACACCCAAGAGGTCCCGGAGAGACTTTGGGCT 120
     P  F  L  E  V  K  V  T  D  T  P [K  R] S [R  R] D  F  G  L
121 TGACTGCGATGAGCACTCCACGGAATCCCGGTGCTGCCGCTACCCCCTCACGGTCGATTT 180
     D  C  D  E  H  S  T  E  S  R  C  C  R  Y  P  L  T  V  D  F
181 TGAAGCCTTTGGATGGGACTGGATTATCGCACCCAAAAGATATAAGGCCAATTACTGCTC 240
     E  A  F  G  W  D  W  I  I  A  P  K  R  Y  K  A  N  Y  C  S
241 AGGAGAGTGTGAATTTGTGTTTTTACAAAAATATCCGCATACTCATCTTGTGCACCAAGC 300
     G  E  C  E  F  V  F  L  Q  K  Y  P  H  T  H  L  V  H  Q  A
301 AAACCCCAGAGGCTCAGCAGGCCCTTGCTGCACTCCGACAAAAATGTCTCCCATTAATAT 360
     N  P  R  G  S  A  G  P  C  C  T  P  T  K  M  S  P  I  N  M
361 GCTATATTTTAATGGCAAAGAACAAATAATATATGGGAAAATTCCAGCCATGGTAGTAGA 420
     L  Y  F  N  G  K  E  Q  I  I  Y  G  K  I  P  A  M  V  V  D
421 CCGCTGTGGGTGCTCATGAGCTTTGCATTAGGTTAGAAACTTCCCAAGTCATGGAAGGTC 480
     R  C  G  C  S  *
481 TTCCCCTCAATTTCGAAACTGTGAATTCCTGCAGCCCGGGGGATCCACTAGTTCTAGAGC 540
541 GGCCGCCACC 550
```

FIG.2a

```
  1 CAAAAAGATCCAGAAGGGATTTTGGTCTTGACTGTGATGAGCACTCAACAGAATCACGAT  60
    [K  R] S [R  R] D  F  G  L  D  C  D  E  H  S  T  E  S  R  C
 61 GCTGTCGTTACCCTCTAACTGTGGATTTTGAAGCTTTTGGATGGGATTGGATTATCGCTC 120
     C  R  Y  P  L  T  V  D  F  E  A  F  G  W  D  W  I  I  A  P
121 CTAAAAGATATAAGGCCAATTACTGCTCTGGAGAGTGTGAATTTGTATTTTTACAAAAAT 180
     K  R  Y  K  A  N  Y  C  S  G  E  C  E  F  V  F  L  Q  K  Y
181 ATCCTCATACTCATCTGGTACACCAAGCAAACCCCAGAGGTTCAGCAGGCCCTTGCTGTA 240
     P  H  T  H  L  V  H  Q  A  N  P  R  G  S  A  G  P  C  C  T
241 CTCCCACAAAGATGTCTCCAATTAATATGCTATATTTTAATGGCAAAGAACAAATAATAT 300
     P  T  K  M  S  P  I  N  M  L  Y  F  N  G  K  E  Q  I  I  Y
301 ATGGGAAAATTCCAGCCATGGTAGTA  326
     G  K  I  P  A  M  V  V
```

FIG.2b

```
GDF-8        SRRDFGLDCDEHSTESRCCRYPLTVDF-EAFGWD-WIIAPKRYKANYCSGECEFVFLQKYP----
GDF-1        RPRRDAEPVLGGGPGGACRARRLYVSF-REVGWHRWVIAPRGFLANYCQGCCALPVALSGSGGPP
BMP-2        REKRQAKHKQRKRLKSSCKRHPLYVDF-SDVGWNDWIVAPPGYHAFYCHGECPFPLADHLNS----
BMP-4        KRSPKHHSQRARKKNKNCRRHSLYVDF-SDVGWNDWIVAPPGYQAFYCHGDCPFPLADHLNS----
Vgr-1        SRGSGSSDYNGSELKTACKKHELYVSF-QDLGWQDWIIAPKGYAANYCDGECSFPLNAHMNA----
OP-1         LRMANVAENSSSDQRQACKKHELYVSF-RDLGWQDWIIAPEGYAAYYCEGECAFPLNSYMNA----
BMP-5        SRMSSVGDYNTSEQKQACKKHELYVSF-RDLGWQDWIIAPEGYAAFYCDGECSFPLNAHMNA----
BMP-3        EQTLKKARRKQWIEPRNCARRYLKVDF-ADIGWSEWIISPKSFDAYYCSGACQFPMPKSLKPS--
MIS          GPGRAQRSAGATAADGPCALRELSVDL----RAERSVLIPETYQANNCQGVCGWPQSDRNPRY--
Inhibin α    ALRLLQRPPEEPAAHANCHRVALNISF-QELGWERWIVYPPSFIFHYCHGGCGLHIPPNLSLPV-
Inhibin βA   HRRRRRGLECDGKV-NICCKKQFFVSF-KDIGWNDWIIAPSGYHANYCEGECPSHIAGTSGSSL-
Inhibin βB   HRIRKRGLECDGRT-NLCCRQQFFIDF-RLIGWNDWIIAPTGYYGNYCEGSCPAYLAGVPGSAS-
TGF-β1       HRRALDTNYCFSSTEKNCCVRQLYIDFRKDLGWK-WIHEPKGYHANFCLGPCPYIWSLD------
TGF-β2       KKRALDAAYCFRNVQDNCCLRPLYIDFKRDLGWK-WIHEPKGYNANFCAGACPYLWSSD------
TGF-β3       KKRALDTNYCFRNLEENCCVRPLYIDFRQDLGWK-WVHEPKGYYANFCSGPCPYLRSAD------

GDF-8        -HTHLVHQANPRG--------SAGPCCT--PTKMSPINMLYF-NGKEQIIYGKIPAMVVDRCGCS

GDF-1        ALNHAVLRALMHA--AAPGAADLPCCV---PARLSPISVLFF-DNSDNVVLRQYEDMVVDECGCR
BMP-2        -TNHAIVQTLVNS----VNSKIPKACCV--PTELSAISMLYL-DENEKVVLKNYQDMVVEGCGCR
BMP-4        -TNHAIVQTLVNS----VNSSIPKACCV--PTELSAISMLYL-DEYDKVVLKNYQEMVVEGCGCR
Vgr-1        -TNHAIVQTLVHL--MNPEYVPKPCCA---PTKLNAISVLYF-DDNSNVILKKYRNMVVRACGCH
OP-1         -TNHAIVQTLVHF---INPETVPKPCCA--PTQLNAISVLYF-DDSSNVILKKYRNMVVRACGCH
BMP-5        -TNHAIVQTLVHL--MFPDHVPKPCCA---PTKLNAISVLYF-DDSSNVILKKYRNMVVRSCGCH
BMP-3        --NHATIQSIVRA-VGVVPGIPEPCCV---PEKMSSLSILFF-DENKNVVLKVYPNMTVESCACR
MIS          -GNHVVLLLKMQA--RGAALARPPCCV---PTAYAGKLLISLSEER--ISAHHVPNMVATECGCR
Inhibin α    -PGAPPTPAQPYS------LLPGAQPCCAALPGTMRPLHVRTTSDGGYSFKYETVPNLLTQHCACI
Inhibin βA   -SFHSTVINHYRMRGHSPFANLKSCCV---PTKLRPMSMLYY-DDGQNIIKKDIQNMIVEECGCS
Inhibin βB   -SFHTAVVNQYRMRGLNPGT-VNSCCI---PTKLSTMSMLYF-DDEYNIVKRDVPNMIVEECGCA
TGF-β1       -TQYSKVLALYNQ--HNPGASAAPCCV---PQALEPLPIVYY-VGRKPKV-EQLSNMIVRSCKCS
TGF-β2       -TQHSRVLSLYNT--INPEASASPCCV---SQDLEPLTILYY-IGKTPKI-EQLSNMIVKSCKCS
TGF-β3       -TTHSTVLGLYNT--LNPEASASPCCV---PQDLEPLTILYY-VGRTPKV-EQLSNMVVKSCKCS
```

| | GDF-1 | GDF-2 | GDF-3 | GDF-5 | GDF-6 | GDF-7 | GDF-8 | GDF-9 | BMP-2 | BMP-4 | Vgr-1 | OP-1 | BMP-5 | BMP-3 | MIS | Inhibin α | Inhibin βA | Inhibin βB | TGF-β1 | TGF-β2 | TGF-β3 |
|---|---|---|---|---|---|---|---|---|---|---|---|---|---|---|---|---|---|---|---|---|---|
| GDF-1     | 100 | — | — | — | — | — | — | — | — | — | — | — | — | — | — | — | — | — | — | — | — |
| GDF-2     | 33  | 100 | — | — | — | — | — | — | — | — | — | — | — | — | — | — | — | — | — | — | — |
| GDF-3     | 50  | 42  | 100 | — | — | — | — | — | — | — | — | — | — | — | — | — | — | — | — | — | — |
| GDF-5     | 46  | 47  | 49  | 100 | — | — | — | — | — | — | — | — | — | — | — | — | — | — | — | — | — |
| GDF-6     | 44  | 51  | 49  | 86  | 100 | — | — | — | — | — | — | — | — | — | — | — | — | — | — | — | — |
| GDF-7     | 48  | 48  | 46  | 80  | 80  | 100 | — | — | — | — | — | — | — | — | — | — | — | — | — | — | — |
| GDF-8     | 35  | 31  | 41  | 37  | 38  | 37  | 100 | — | — | — | — | — | — | — | — | — | — | — | — | — | — |
| GDF-9     | 27  | 32  | 33  | 33  | 34  | 33  | 27  | 100 | — | — | — | — | — | — | — | — | — | — | — | — | — |
| BMP-2     | 42  | 52  | 53  | 57  | 57  | 57  | 41  | 33  | 100 | — | — | — | — | — | — | — | — | — | — | — | — |
| BMP-4     | 43  | 51  | 50  | 57  | 56  | 57  | 38  | 34  | 92  | 100 | — | — | — | — | — | — | — | — | — | — | — |
| Vgr-1     | 46  | 55  | 53  | 51  | 53  | 52  | 45  | 31  | 61  | 60  | 100 | — | — | — | — | — | — | — | — | — | — |
| OP-1      | 47  | 52  | 50  | 51  | 53  | 53  | 42  | 30  | 60  | 58  | 87  | 100 | — | — | — | — | — | — | — | — | — |
| BMP-5     | 46  | 55  | 50  | 52  | 54  | 52  | 42  | 31  | 61  | 59  | 91  | 88  | 100 | — | — | — | — | — | — | — | — |
| BMP-3     | 42  | 34  | 42  | 47  | 46  | 46  | 38  | 29  | 48  | 47  | 44  | 42  | 43  | 100 | — | — | — | — | — | — | — |
| MIS       | 34  | 20  | 22  | 27  | 26  | 25  | 31  | 21  | 27  | 27  | 24  | 27  | 24  | 30  | 100 | — | — | — | — | — | — |
| Inhibin α | 23  | 20  | 25  | 24  | 27  | 26  | 26  | 27  | 22  | 22  | 25  | 24  | 24  | 29  | 18  | 100 | — | — | — | — | — |
| Inhibin βA| 37  | 32  | 42  | 40  | 43  | 41  | 38  | 30  | 42  | 41  | 44  | 43  | 43  | 36  | 24  | 26  | 100 | — | — | — | — |
| Inhibin βB| 35  | 25  | 41  | 37  | 39  | 36  | 42  | 31  | 42  | 42  | 41  | 42  | 37  | 37  | 25  | 25  | 63  | 100 | — | — | — |
| TGF-β1    | 33  | 26  | 36  | 33  | 35  | 36  | 34  | 23  | 35  | 34  | 35  | 34  | 34  | 32  | 28  | 23  | 41  | 35  | 100 | — | — |
| TGF-β2    | 32  | 28  | 31  | 34  | 36  | 35  | 37  | 25  | 34  | 33  | 37  | 38  | 35  | 32  | 23  | 22  | 37  | 34  | 74  | 100 | — |
| TGF-β3    | 33  | 30  | 32  | 37  | 38  | 38  | 37  | 25  | 36  | 35  | 39  | 38  | 36  | 32  | 25  | 24  | 36  | 37  | 78  | 82  | 100 |

```
   1 GTCTCTCGGACGGTACATGCACTAATATTTCACTTGGCATTACTCAAAAGCAAAAAGAAG    60
  61 AAATAAGAACAAGGGAAAAAAAAAGATTGTGCTGATTTTTAAAATGATGCAAAAACTGCA   120
                                              M  M  Q  K  L  Q
 121 AATGTATGTTTATATTTACCTGTTCATGCTGATTGCTGCTGGCCCAGTGGATCTAAATGA   180
      M  Y  V  Y  I  Y  L  F  M  L  I  A  A  G  P  V  D  L  N  E
 181 GGGCAGTGAGAGAGAAGAAAATGTGGAAAAAGAGGGGCTGTGTAATGCATGTGCCGTGGAG   240
      G  S  E  R  E  E  N  V  E  K  E  G  L  C  N  A  C  A  W  R
 241 ACAAAACACGAGGTACTCCAGAATAGAAGCCATAAAAATTCAAATCCTCAGTAAGCTGCG   300
      Q  N  T  R  Y  S  R  I  E  A  I  K  I  Q  I  L  S  K  L  R
 301 CCTGGAAACAGCTCCTAACATCAGCAAAGATGCTATAAGACAACTTCTGCCAAGAGCGCC   360
      L  E  T  A  P  [N  I  S] K  D  A  I  R  Q  L  L  P  R  A  P
 361 TCCACTCCGGGAACTGATCGATCAGTACGACGTCCAGAGGGATGACAGCAGTGATGGCTC   420
      P  L  R  E  L  I  D  Q  Y  D  V  Q  R  D  D  S  S  D  G  S
 421 TTTGGAAGATGACGATTATCACGCTACCACGGAAACAATCATTACCATGCCTACAGAGTC   480
      L  E  D  D  D  Y  H  A  T  T  E  T  I  I  T  M  P  T  E  S
 481 TGACTTTCTAATGCAAGCGGATGGCAAGCCCAAATGTTGCTTTTTTAAATTTAGCTCTAA   540
      D  F  L  M  Q  A  D  G  K  P  K  C  C  F  F  K  F  S  S  K
 541 AATACAGTACAACAAAGTAGTAAAAGCCCAACTGTGGATATATCTCAGACCCGTCAAGAC   600
      I  Q  Y  N  K  V  V  K  A  Q  L  W  I  Y  L  R  P  V  K  T
 601 TCCTACAACAGTGTTTGTGCAAATCCTGAGACTCATCAAACCCATGAAAGACGGTACAAG   660
      P  T  T  V  F  V  Q  I  L  R  L  I  K  P  M  K  D  G  T  R
 661 GTATACTGGAATCCGATCTCTGAAACTTGACATGAGCCCAGGCACTGGTATTTGGCAGAG   720
      Y  T  G  I  R  S  L  K  L  D  M  S  P  G  T  G  I  W  Q  S
 721 TATTGATGTGAAGACAGTGTTGCAAAATTGGCTCAAACAGCCTGAATCCAACTTAGGCAT   780
      I  D  V  K  T  V  L  Q  N  W  L  K  Q  P  E  S  N  L  G  I
 781 TGAAATCAAAGCTTTGGATGAGAATGGCCATGATCTTGCTGTAACCTTCCCAGGACCAGG   840
      E  I  K  A  L  D  E  N  G  H  D  L  A  V  T  F  P  G  P  G
 841 AGAAGATGGGCTGAATCCCTTTTTAGAAGTCAAGGTGACAGACACACCCAAGAGGTCCCG   900
      E  D  G  L  N  P  F  L  E  V  K  V  T  D  T  P  K [R  S  R
 901 GAGAGACTTTGGGCTTGACTGCGATGAGCACTCCACGGAATCCCGGTGCTGCCGCTACCC   960
      R] D  F  G  L  D  C  D  E  H  S  T  E  S  R  C  C  R  Y  P
 961 CCTCACGGTCGATTTTGAAGCCTTTGGATGGGACTGGATTATCGCACCCAAAAGATATAA  1020
      L  T  V  D  F  E  A  F  G  W  D  W  I  I  A  P  K  R  Y  K
1021 GGCCAATTACTGCTCAGGAGAGTGTGAATTTGTGTTTTTACAAAAATATCCGCATACTCA  1080
      A  N  Y  C  S  G  E  C  E  F  V  F  L  Q  K  Y  P  H  T  H
1081 TCTTGTGCACCAAGCAAACCCCAGAGGCTCAGCAGGCCCTTGCTGCACTCCGACAAAAAT  1140
      L  V  H  Q  A  N  P  R  G  S  A  G  P  C  C  T  P  T  K  M
1141 GTCTCCCATTAATATGCTATATTTTAATGGCAAAGAACAAATAATATATGGGAAAATTCC  1200
      S  P  I  N  M  L  Y  F  N  G  K  E  Q  I  I  Y  G  K  I  P
1201 AGCCATGGTAGTAGACCGCTGTGGGTGCTCATGAGCTTTGCATTAGGTTAGAAACTTCCC  1260
      A  M  V  V  D  R  C  G  C  S  *
```

FIG. 5a

```
1261  AAGTCATGGAAGGTCTTCCCCTCAATTTCGAAACTGTGAATTCAAGCACCACAGGCTGTA  1320
1321  GGCCTTGAGTATGCTCTAGTAACGTAAGCACAAGCTACAGTGTATGAACTAAAAGAGAGA  1380
1381  ATAGATGCAATGGTTGGCATTCAACCACCAAAATAAACCATACTATAGGATGTTGTATGA  1440
1441  TTTCCAGAGTTTTTGAAATAGATGGAGATCAAATTACATTTATGTCCATATATGTATATT  1500
1501  ACAACTACAATCTAGGCAAGGAAGTGAGAGCACATCTTGTGGTCTGCTGAGTTAGGAGGG  1560
1561  TATGATTAAAAGGTAAAGTCTTATTTCCTAACAGTTTCACTTAATATTTACAGAAGAATC  1620
1621  TATATGTAGCCTTTGTAAAGTGTAGGATTGTTATCATTTAAAAACATCATGTACACTTAT  1680
1681  ATTTGTATTGTATACTTGGTAAGATAAAATTCCACAAAGTAGGAATGGGGCCTCACATAC  1740
1741  ACATTGCCATTCCTATTATAATTGGACAATCCACCACGGTGCTAATGCAGTGCTGAATGG  1800
1801  CTCCTACTGGACCTCTCGATAGAACACTCTACAAAGTACGAGTCTCTCTCTCCCTTCCAG  1860
1861  GTGCATCTCCACACACACAGCACTAAGTGTTCAATGCATTTTCTTTAAGGAAAGAAGAAT  1920
1921  CTTTTTTTCTAGAGGTCAACTTTCAGTCAACTCTAGCACAGCGGGAGTGACTGCTGCATC  1980
1981  TTAAAAGGCAGCCAAACAGTATTCATTTTTAATCTAAATTTCAAAATCACTGTCTGCCT   2040
2041  TTATCACATGGCAATTTTGTGGTAAAATAATGGAAATGACTGGTTCTATCAATATTGTAT  2100
2101  AAAAGACTCTGAAACAATTACATTTATATAATATGTATACAATATTGTTTTGTAAATAAG  2160
2161  TGTCTCCTTTTATATTTACTTTGGTATATTTTTACACTAATGAAATTTCAAATCATTAAA  2220
2221  GTACAAAGACATGTCATGTATCACAAAAAAGGTGACTGCTTCTATTTCAGAGTGAATTAG  2280
2281  CAGATTCAATAGTGGTCTTAAAACTCTGTATGTTAAGATTAGAAGGTTATATTACAATCA  2340
2341  ATTTATGTATTTTTTACATTATCAACTTATGGTTTCATGGTGGCTGTATCTATGAATGTG  2400
2401  GCTCCCAGTCAAATTTCAATGCCCCACCATTTTAAAAATTACAAGCATTACTAAACATAC  2460
2461  CAACATGTATCTAAAGAAATACAAATATGGTATCTCAATAACAGCTACTTTTTATTTTA   2520
2521  TAATTTGACAATGAATACATTTCTTTTATTTACTTCAGTTTTATAAATTGGAACTTTGTT  2580
2581  TATCAAATGTATTGTACTCATAGCTAAATGAAATTATTTCTTACATAAAAATGTGTAGAA  2640
2641  ACTATAAATTAAAGTGTTTTCACATTTTTGAAAGGC  2676
```

FIG.5b

```
   1  AAGAAAAGTAAAAGGAAGAAACAAGAACAAGAAAAAAGATTATATTGATTTTAAAATCAT    60
                                                                M
  61  GCAAAAACTGCAACTCTGTGTTTATATTTACCTGTTTATGCTGATTGTTGCTGGTCCAGT   120
       Q  K  L  Q  L  C  V  Y  I  Y  L  F  M  L  I  V  A  G  P  V
 121  GGATCTAAATGAGAACAGTGAGCAAAAAGAAAATGTGGAAAAAGAGGGGCTGTGTAATGC   180
       D  L  N  E  N  S  E  Q  K  E  N  V  E  K  E  G  L  C  N  A
 181  ATGTACTTGGAGACAAAACACTAAATCTTCAAGAATAGAAGCCATTAAGATACAAATCCT   240
       C  T  W  R  Q  N  T  K  S  S  R  I  E  A  I  K  I  Q  I  L
 241  CAGTAAACTTCGTCTGGAAACAGCTCCTAACATCAGCAAAGATGTTATAAGACAACTTTT   300
       S  K  L  R  L  E  T  A  P [N  I  S] K  D  V  I  R  Q  L  L
 301  ACCCAAAGCTCCTCCACTCCGGGAACTGATTGATCAGTATGATGTCCAGAGGGATGACAG   360
       P  K  A  P  P  L  R  E  L  I  D  Q  Y  D  V  Q  R  D  D  S
 361  CAGCGATGGCTCTTTGGAAGATGACGATTATCACGCTACAACGGAAACAATCATTACCAT   420
       S  D  G  S  L  E  D  D  D  Y  H  A  T  T  E  T  I  I  T  M
 421  GCCTACAGAGTCTGATTTTCTAATGCAAGTGGATGGAAAACCCAAATGTTGCTTCTTTAA   480
       P  T  E  S  D  F  L  M  Q  V  D  G  K  P  K  C  C  F  F  K
 481  ATTTAGCTCTAAAATACAATACAATAAAGTAGTAAAGGCCCAACTATGGATATATTTGAG   540
       F  S  S  K  I  Q  Y  N  K  V  V  K  A  Q  L  W  I  Y  L  R
 541  ACCCGTCGAGACTCCTACAACAGTGTTTGTGCAAATCCTGAGACTCATCAAACCTATGAA   600
       P  V  E  T  P  T  T  V  F  V  Q  I  L  R  L  I  K  P  M  K
 601  AGACGGTACAAGGTATACTGGAATCCGATCTCTGAAACTTGACATGAACCCAGGCACTGG   660
       D  G  T  R  Y  T  G  I  R  S  L  K  L  D  M  N  P  G  T  G
 661  TATTTGGCAGAGCATTGATGTGAAGACAGTGTTGCAAAATTGGCTCAAACAACCTGAATC   720
       I  W  Q  S  I  D  V  K  T  V  L  Q  N  W  L  K  Q  P  E  S
 721  CAACTTAGGCATTGAAATAAAAGCTTTAGATGAGAATGGTCATGATCTTGCTGTAACCTT   780
       N  L  G  I  E  I  K  A  L  D  E  N  G  H  D  L  A  V  T  F
 781  CCCAGGACCAGGAGAAGATGGGCTGAATCCGTTTTTAGAGGTCAAGGTAACAGACACACC   840
       P  G  P  G  E  D  G  L  N  P  F  L  E  V  K  V  T  D  T  P
 841  AAAAAAGATCCAGAAGGGATTTTGGTCTTGACTGTGATGAGCACTCAACAGAATCACGATG   900
       K [R  S  R  R] D  F  G  L  D  C  D  E  H  S  T  E  S  R  C
 901  CTGTCGTTACCCTCTAACTGTGGATTTTGAAGCTTTTGGATGGGATTGGATTATCGCTCC   960
       C  R  Y  P  L  T  V  D  F  E  A  F  G  W  D  W  I  I  A  P
 961  TAAAAGATATAAGGCCAATTACTGCTCTGGAGAGTGTGAATTTGTATTTTTACAAAAATA  1020
       K  R  Y  K  A  N  Y  C  S  G  E  C  E  F  V  F  L  Q  K  Y
1021  TCCTCATACTCATCTGGTACACCAAGCAAACCCCAGAGGTTCAGCAGGCCCTTGCTGTAC  1080
       P  H  T  H  L  V  H  Q  A  N  P  R  G  S  A  G  P  C  C  T
1081  TCCCACAAAGATGTCTCCAATTAATATGCTATATTTTAATGGCAAAGAACAAATAATATA  1140
       P  T  K  M  S  P  I  N  M  L  Y  F  N  G  K  E  Q  I  I  Y
1141  TGGGAAAATTCCAGCGATGGTAGTAGACCGCTGTGGGTGCTCATGAGATTTATATTAAGC  1200
       G  K  I  P  A  M  V  V  D  R  C  G  C  S  *
```

FIG.5c

```
1201  GTTCATAACTTCCTAAAACATGGAAGGTTTTCCCCTCAACAATTTTGAAGCTGTGAAATT  1260
1261  AAGTACCACAGGCTATAGGCCTAGAGTATGCTACAGTCACTTAAGCATAAGCTACAGTAT  1320
1321  GTAAACTAAAAGGGGGAATATATGCAATGGTTGGCATTTAACCATCCAAACAAATCATAC  1380
1381  AAGAAAGTTTTATGATTTCCAGAGTTTTTGAGCTAGAAGGAGATCAAATTACATTTATGT  1440
1441  TCCTATATATTACAACATCGGCGAGGAAATGAAAGCGATTCTCCTTGAGTTCTGATGAAT  1500
1501  TAAAGGAGTATGCTTTAAAGTCTATTTCTTTAAAGTTTTGTTTAATATTTACAGAAAAAT  1560
1561  CCACATACAGTATTGGTAAAATGCAGGATTGTTATATACCATCATTCGAATCATCCTTAA  1620
1621  ACACTTGAATTTATATTGTATGGTAGTATACTTGGTAAGATAAAATTCCACAAAAATAGG  1680
1681  GATGGTGCAGCATATGCAATTTCCATTCCTATTATAATTGACACAGTACATTAACAATCC  1740
1741  ATGCCAACGGTGCTAATACGATAGGCTGAATGTCTGAGGCTACCAGGTTTATCACATAAA  1800
1801  AAACATTCAGTAAAATAGTAAGTTTCTCTTTTCTTCAGGTGCATTTTCCTACACCTCCAA  1860
1861  ATGAGGAATGGATTTTCTTTAATGTAAGAAGAATCATTTTTCTAGAGGTTGGCTTTCAAT  1920
1921  TCTGTAGCATACTTGGAGAAACTGCATTATCTTAAAAGGCAGTCAAATGGTGTTTGTTTT  1980
1981  TATCAAAATGTCAAAATAACATACTTGGAGAAGTATGTAATTTTGTCTTTGGAAAATTAC  2040
2041  AACACTGCCTTTGCAACACTGCAGTTTTTATGGTAAAATAATAGAAATGATCGACTCTAT  2100
2101  CAATATTGTATAAAAAGACTGAAACAATGCATTTATATAATATGTATACAATATTGTTTT  2160
2161  GTAAATAAGTGTCTCCTTTTTTATTTACTTTGGTATATTTTTACACTAAGGACATTTCAA  2220
2221  ATTAAGTACTAAGGCACAAAGACATGTCATGCATCACAGAAAAGCAACTACTTATATTTC  2280
2281  AGAGCAAATTAGCAGATTAAATAGTGGTCTTAAAACTCCATATGTTAATGATTAGATGGT  2340
2341  TATATTACAATCATTTATATTTTTTTACATGATTAACATTCACTTATGGATTCATGATG  2400
2401  GCTGTATAAAGTGAATTTGAAATTTCAATGGTTTACTGTCATTGTGTTTAAATCTCAACG  2460
2461  TTCCATTATTTTAATACTTGCAAAAACATTACTAAGTATACCAAAATAATTGACTCTATT  2520
2521  ATCTGAAATGAAGAATAAACTGATGCTATCTCAACAATAACTGTTACTTTTATTTTATAA  2580
2581  TTTGATAATGAATATATTTCTGCATTTATTTACTTCTGTTTTGTAAATTGGGATTTTGTT  2640
2641  AATCAAATTTATTGTACTATGACTAAATGAAATTATTTCTTACATCTAATTTGTAGAAAC  2700
2701  AGTATAAGTTATATTAAAGTGTTTTCACATTTTTTTGAAAGAC  2743
```

FIG.5d

```
  1  MMQKLQMYVYIYLFMLIAAGPVDLNEGSEREENVEKEGLCNACAWRQNTR   50
     |||||  |||||||||| |||||||| || |||||||||||| |||||
  1  MQKLQLCVYIYLFMLIVAGPVDLNENSEQKENVEKEGLCNACTWRQNTK    49

51  YSRIEAIKIQILSKLRLETAPNISKDAIRQLLPRAPPLRELIDQYDVQRD  100
     ||||||||||||||||||||||||| |||||| ||||||||||||||||
 50  SSRIEAIKIQILSKLRLETAPNISKDVIRQLLPKAPPLRELIDQYDVQRD   99

101  DSSDGSLEDDDYHATTETIITMPTESDFLMQADGKPKCCFFKFSSKIQYN  150
     |||||||||||||||||||||||||||||| ||||||||||||||||||
100  DSSDGSLEDDDYHATTETIITMPTESDFLMQVDGKPKCCFFKFSSKIQYN  149

151  KVVKAQLWIYLRPVKTPTTVFVQILRLIKPMKDGTRYTGIRSLKLDMSPG  200
     ||||||||||||| |||||||||||||||||||||||||||||||| ||
150  KVVKAQLWIYLRPVETPTTVFVQILRLIKPMKDGTRYTGIRSLKLDMNPG  199

201  TGIWQSIDVKTVLQNWLKQPESNLGIEIKALDENGHDLAVTFPGPGEDGL  250
     |||||||||||||||||||||||||||||||||||||||||||||||||
200  TGIWQSIDVKTVLQNWLKQPESNLGIEIKALDENGHDLAVTFPGPGEDGL  249

251  NPFLEVKVTDTPKRSRRDFGLDCDEHSTESRCCRYPLTVDFEAFGWDWII  300
     |||||||||||||||||||||||||||||||||||||||||||||||||
250  NPFLEVKVTDTPKRSRRDFGLDCDEHSTESRCCRYPLTVDFEAFGWDWII  299

301  APKRYKANYCSGECEFVFLQKYPHTHLVHQANPRGSAGPCCTPTKMSPIN  350
     |||||||||||||||||||||||||||||||||||||||||||||||||
300  APKRYKANYCSGECEFVFLQKYPHTHLVHQANPRGSAGPCCTPTKMSPIN  349

351  MLYFNGKEQIIYGKIPAMVVDRCGCS  376
     ||||||||||||||||||||||||||
350  MLYFNGKEQIIYGKIPAMVVDRCGCS  375
```

FIG.7 ns appl
5,827,733

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 35 base pairs
        ( B ) TYPE: nucleic acid ( C ) STRANDEDNESS: single
( D ) TOPOLOGY: linear ( i i ) MOLECULE TYPE: Genomic DNA ( v i i ) IMMEDIATE SOURCE:
( B ) CLONE: SJL141

( i x ) FEATURE:
( A ) NAME/KEY: Modified Base
( B ) LOCATION: 1...35
( D ) OTHER INFORMATION: /note= "N=inosine"

( x i ) SEQUENCE DESCRIPTION: SEQ ID NO:1:

CCGGAATTCG GNTGGVANRA YTGGRTNRTN KCNCC 35

( 2 ) INFORMATION FOR SEQ ID NO:2:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: Genomic DNA ( v i i ) IMMEDIATE SOURCE:
( B ) CLONE: SJL147

( i x ) FEATURE:
( A ) NAME/KEY: CDS
( B ) LOCATION: 1...33
( C ) OTHER INFORMATION: /note= "N-inosine"

( x i ) SEQUENCE DESCRIPTION: SEQ ID NO:2:

CCGGAATTCR CANSCRCARC TNTCNACNRY CAT 33

( 2 ) INFORMATION FOR SEQ ID NO:3:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( v i i ) IMMEDIATE SOURCE:
( B ) CLONE: ACM13

( i x ) FEATURE:
( A ) NAME/KEY: CDS
( B ) LOCATION: 1...32

( x i ) SEQUENCE DESCRIPTION: SEQ ID NO:3:

CGCGGATCCA GAAGTCAAGG TGACAGACAC AC 32

( 2 ) INFORMATION FOR SEQ ID NO:4:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: Genomic DNA ( v i i ) IMMEDIATE SOURCE:
( B ) CLONE: ACM14

( i x ) FEATURE:
( A ) NAME/KEY: CDS
( B ) LOCATION: 1...33

( x i ) SEQUENCE DESCRIPTION: SEQ ID NO:4:

CGCGGATCCT CCTCATGAGC ACCCACAGCG GTC                33

( 2 ) INFORMATION FOR SEQ ID NO:5:

( i ) SEQUENCE CHARACTERISTICS:
    ( A ) LENGTH: 550 base pairs
    ( B ) TYPE: nucleic acid
    ( C ) STRANDEDNESS: single
    ( D ) TOPOLOGY: linear ( v i i ) IMMEDIATE SOURCE:
    ( B ) CLONE: mouse GDF-8

( i x ) FEATURE:
    ( A ) NAME/KEY: CDS
    ( B ) LOCATION: 59...436

( x i ) SEQUENCE DESCRIPTION: SEQ ID NO:5:

TTAAGGTAGG AAGGATTTCA GGCTCTATTT ACATAATTGT TCTTTCCTTT TCACACAG                58

| AAT | CCC | TTT | TTA | GAA | GTC | AAG | GTG | ACA | GAC | ACA | CCC | AAG | AGG | TCC | CGG | 106 |
| Asn | Pro | Phe | Leu | Glu | Val | Lys | Val | Thr | Asp | Thr | Pro | Lys | Arg | Ser | Arg | |
| 1 | | | | 5 | | | | | 10 | | | | | 15 | | |

| AGA | GAC | TTT | GGG | CTT | GAC | TGC | GAT | GAG | CAC | TCC | ACG | GAA | TCC | CGG | TGC | 154 |
| Arg | Asp | Phe | Gly | Leu | Asp | Cys | Asp | Glu | His | Ser | Thr | Glu | Ser | Arg | Cys | |
| | | | 20 | | | | | 25 | | | | | 30 | | | |

| TGC | CGC | TAC | CCC | CTC | ACG | GTC | GAT | TTT | GAA | GCC | TTT | GGA | TGG | GAC | TGG | 202 |
| Cys | Arg | Tyr | Pro | Leu | Thr | Val | Asp | Phe | Glu | Ala | Phe | Gly | Trp | Asp | Trp | |
| | | 35 | | | | | 40 | | | | | 45 | | | | |

| ATT | ATC | GCA | CCC | AAA | AGA | TAT | AAG | GCC | AAT | TAC | TGC | TCA | GGA | GAG | TGT | 250 |
| Ile | Ile | Ala | Pro | Lys | Arg | Tyr | Lys | Ala | Asn | Tyr | Cys | Ser | Gly | Glu | Cys | |
| | | | 50 | | | | 55 | | | | | 60 | | | | |

| GAA | TTT | GTG | TTT | TTA | CAA | AAA | TAT | CCG | CAT | ACT | CAT | CTT | GTG | CAC | CAA | 298 |
| Glu | Phe | Val | Phe | Leu | Gln | Lys | Tyr | Pro | His | Thr | His | Leu | Val | His | Gln | |
| 65 | | | | | 70 | | | | | 75 | | | | | 80 | |

| GCA | AAC | CCC | AGA | GGC | TCA | GCA | GGC | CCT | TGC | TGC | ACT | CCG | ACA | AAA | ATG | 346 |
| Ala | Asn | Pro | Arg | Gly | Ser | Ala | Gly | Pro | Cys | Cys | Thr | Pro | Thr | Lys | Met | |
| | | | | 85 | | | | | 90 | | | | | 95 | | |

| TCT | CCC | ATT | AAT | ATG | CTA | TAT | TTT | AAT | GGC | AAA | GAA | CAA | ATA | ATA | TAT | 394 |
| Ser | Pro | Ile | Asn | Met | Leu | Tyr | Phe | Asn | Gly | Lys | Glu | Gln | Ile | Ile | Tyr | |
| | | | 100 | | | | | 105 | | | | | 110 | | | |

| GGG | AAA | ATT | CCA | GCC | ATG | GTA | GTA | GAC | CGC | TGT | GGG | TGC | TCA | TGAGCTTTGC | | 446 |
| Gly | Lys | Ile | Pro | Ala | Met | Val | Val | Asp | Arg | Cys | Gly | Cys | Ser | | | |
| | | 115 | | | | | 120 | | | | | 125 | | | | |

ATTAGGTTAG AAACTTCCCA AGTCATGGAA GGTCTTCCCC TCAATTTCGA AACTGTGAAT                506

TCCTGCAGCC CGGGGGATCC ACTAGTTCTA GAGCGGCCGC CACC                550

( 2 ) INFORMATION FOR SEQ ID NO:6:

( i ) SEQUENCE CHARACTERISTICS:
    ( A ) LENGTH: 126 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:6:

| Asn | Pro | Phe | Leu | Glu | Val | Lys | Val | Thr | Asp | Thr | Pro | Lys | Arg | Ser | Arg |
| 1 | | | | 5 | | | | | 10 | | | | | 15 | |

| Arg | Asp | Phe | Gly | Leu | Asp | Cys | Asp | Glu | His | Ser | Thr | Glu | Ser | Arg | Cys |
| | | | 20 | | | | | 25 | | | | | 30 | | |

| Cys | Arg | Tyr | Pro | Leu | Thr | Val | Asp | Phe | Glu | Ala | Phe | Gly | Trp | Asp | Trp |
| | | 35 | | | | | 40 | | | | | 45 | | | |

```
Ile  Ile  Ala  Pro  Lys  Arg  Tyr  Lys  Ala  Asn  Tyr  Cys  Ser  Gly  Glu  Cys
     50                  55                       60

Glu  Phe  Val  Phe  Leu  Gln  Lys  Tyr  Pro  His  Thr  His  Leu  Val  His  Gln
65                       70                  75                            80

Ala  Asn  Pro  Arg  Gly  Ser  Ala  Gly  Pro  Cys  Cys  Thr  Pro  Thr  Lys  Met
                    85                       90                       95

Ser  Pro  Ile  Asn  Met  Leu  Tyr  Phe  Asn  Gly  Lys  Glu  Gln  Ile  Ile  Tyr
               100                      105                      110

Gly  Lys  Ile  Pro  Ala  Met  Val  Val  Asp  Arg  Cys  Gly  Cys  Ser
               115                 120                      125
```

( 2 ) INFORMATION FOR SEQ ID NO:7:

( i ) SEQUENCE CHARACTERISTICS:
        ( A ) LENGTH: 326 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: human GDF-8

( i x ) FEATURE:
        ( A ) NAME/KEY: CDS
        ( B ) LOCATION: 3...326

( x i ) SEQUENCE DESCRIPTION: SEQ ID NO:7:

```
CA  AAA  AGA  TCC  AGA  AGG  GAT  TTT  GGT  CTT  GAC  TGT  GAT  GAG  CAC  TCA        47
    Lys  Arg  Ser  Arg  Arg  Asp  Phe  Gly  Leu  Asp  Cys  Asp  Glu  His  Ser
    1              5                        10                            15

ACA  GAA  TCA  CGA  TGC  TGT  CGT  TAC  CCT  CTA  ACT  GTG  GAT  TTT  GAA  GCT       95
Thr  Glu  Ser  Arg  Cys  Cys  Arg  Tyr  Pro  Leu  Thr  Val  Asp  Phe  Glu  Ala
                    20                       25                       30

TTT  GGA  TGG  GAT  TGG  ATT  ATC  GCT  CCT  AAA  AGA  TAT  AAG  GCC  AAT  TAC      143
Phe  Gly  Trp  Asp  Trp  Ile  Ile  Ala  Pro  Lys  Arg  Tyr  Lys  Ala  Asn  Tyr
                    35                       40                       45

TGC  TCT  GGA  GAG  TGT  GAA  TTT  GTA  TTT  TTA  CAA  AAA  TAT  CCT  CAT  ACT      191
Cys  Ser  Gly  Glu  Cys  Glu  Phe  Val  Phe  Leu  Gln  Lys  Tyr  Pro  His  Thr
               50                  55                       60

CAT  CTG  GTA  CAC  CAA  GCA  AAC  CCC  AGA  GGT  TCA  GCA  GGC  CCT  TGC  TGT      239
His  Leu  Val  His  Gln  Ala  Asn  Pro  Arg  Gly  Ser  Ala  Gly  Pro  Cys  Cys
          65                       70                       75

ACT  CCC  ACA  AAG  ATG  TCT  CCA  ATT  AAT  ATG  CTA  TAT  TTT  AAT  GGC  AAA      287
Thr  Pro  Thr  Lys  Met  Ser  Pro  Ile  Asn  Met  Leu  Tyr  Phe  Asn  Gly  Lys
80                            85                  90                       95

GAA  CAA  ATA  ATA  TAT  GGG  AAA  ATT  CCA  GCG  ATG  GTA  GTA                     326
Glu  Gln  Ile  Ile  Tyr  Gly  Lys  Ile  Pro  Ala  Met  Val  Val
                    100                 105
```

( 2 ) INFORMATION FOR SEQ ID NO:8:

( i ) SEQUENCE CHARACTERISTICS:
        ( A ) LENGTH: 108 amino acids
        ( B ) TYPE: amino acid
        ( D ) TOPOLOGY: linear ( i i i ) MOLECULE TYPE: protein ( v ) FRAGMENT TYPE: internal ( x i ) SEQUENCE DESCRIPTION: SEQ ID NO:8:

```
Lys  Arg  Ser  Arg  Arg  Asp  Phe  Gly  Leu  Asp  Cys  Asp  Glu  His  Ser  Thr
1                   5                        10                            15

Glu  Ser  Arg  Cys  Cys  Arg  Tyr  Pro  Leu  Thr  Val  Asp  Phe  Glu  Ala  Phe
```

|  | 20 |  |  |  |  | 25 |  |  |  |  | 30 |  |  |  |
|---|---|---|---|---|---|---|---|---|---|---|---|---|---|---|
| Gly | Trp | Asp<br>35 | Trp | Ile | Ile | Ala | Pro<br>40 | Lys | Arg | Tyr | Lys | Ala<br>45 | Asn | Tyr | Cys |
| Ser | Gly<br>50 | Glu | Cys | Glu | Phe | Val<br>55 | Phe | Leu | Gln | Lys | Tyr<br>60 | Pro | His | Thr | His |
| Leu<br>65 | Val | His | Gln | Ala | Asn<br>70 | Pro | Arg | Gly | Ser | Ala<br>75 | Gly | Pro | Cys | Cys | Thr<br>80 |
| Pro | Thr | Lys | Met | Ser<br>85 | Pro | Ile | Asn | Met | Leu<br>90 | Tyr | Phe | Asn | Gly | Lys<br>95 | Glu |
| Gln | Ile | Ile | Tyr<br>100 | Gly | Lys | Ile | Pro | Ala<br>105 | Met | Val | Val |

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: SJL141

( i x ) FEATURE:
        ( A ) NAME/KEY: Peptide
        ( B ) LOCATION: 1...9
        ( D ) OTHER INFORMATION: /note= "Xaa at position 3=His, Gln, Asn
            Lys, Asp or Glu; Xaa at position 4=Asp or Asn; Xaa at
            positions 6 and 7=Val, Ile or Met; Ala = Xaa at position
            8=Ala or Ser"

( x i ) SEQUENCE DESCRIPTION: SEQ ID NO:9:

Gly Trp Xaa Xaa Trp Xaa Xaa Xaa Pro
     1                 5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v i i ) IMMEDIATE SOURCE:
        ( B ) CLONE: SJL147

( i x ) FEATURE:
        ( A ) NAME/KEY: Peptide
        ( B ) LOCATION: 1...8
        ( D ) OTHER INFORMATION: /note= "Xaa at position 2=Ile, Val, Met
            Thr or Ala; Xaa at position 4=Asp or Glu; Xaa at position
            7=Gly or Ala"

( x i ) SEQUENCE DESCRIPTION: SEQ ID NO:10:

Met Xaa Val Xaa Ser Cys Xaa Cys
     1              5

( 2 ) INFORMATION FOR SEQ ID NO:11:

( i ) SEQUENCE CHARACTERISTICS:
        ( A ) LENGTH: 2676 base pairs
        ( B ) TYPE: nucleic acid
        ( C ) STRANDEDNESS: single
        ( D ) TOPOLOGY: linear ( i i ) MOLECULE TYPE: Genomic DNA ( v i i ) IMMEDIATE SOURCE:

( B ) CLONE: Murine GDF-8

( i x ) FEATURE:
    ( A ) NAME/KEY: CDS
    ( B ) LOCATION: 104...1231

( x i ) SEQUENCE DESCRIPTION: SEQ ID NO:11:

```
GTCTCTCGGA CGGTACATGC ACTAATATTT CACTTGGCAT TACTCAAAAG CAAAAAGAAG        60

AAATAAGAAC AAGGGAAAAA AAAAGATTGT GCTGATTTTT AAA ATG ATG CAA AAA        115
                                                  Met Met Gln Lys
                                                   1

CTG CAA ATG TAT GTT TAT ATT TAC CTG TTC ATG CTG ATT GCT GCT GGC        163
Leu Gln Met Tyr Val Tyr Ile Tyr Leu Phe Met Leu Ile Ala Ala Gly
  5              10                  15                      20

CCA GTG GAT CTA AAT GAG GGC AGT GAG AGA GAA GAA AAT GTG GAA AAA        211
Pro Val Asp Leu Asn Glu Gly Ser Glu Arg Glu Glu Asn Val Glu Lys
                 25                  30                      35

GAG GGG CTG TGT AAT GCA TGT GCG TGG AGA CAA AAC ACG AGG TAC TCC        259
Glu Gly Leu Cys Asn Ala Cys Ala Trp Arg Gln Asn Thr Arg Tyr Ser
             40                  45                  50

AGA ATA GAA GCC ATA AAA ATT CAA ATC CTC AGT AAG CTG CGC CTG GAA        307
Arg Ile Glu Ala Ile Lys Ile Gln Ile Leu Ser Lys Leu Arg Leu Glu
         55                  60                  65

ACA GCT CCT AAC ATC AGC AAA GAT GCT ATA AGA CAA CTT CTG CCA AGA        355
Thr Ala Pro Asn Ile Ser Lys Asp Ala Ile Arg Gln Leu Leu Pro Arg
     70                  75                  80

GCG CCT CCA CTC CGG GAA CTG ATC GAT CAG TAC GAC GTC CAG AGG GAT        403
Ala Pro Pro Leu Arg Glu Leu Ile Asp Gln Tyr Asp Val Gln Arg Asp
 85                  90                  95                     100

GAC AGC AGT GAT GGC TCT TTG GAA GAT GAC GAT TAT CAC GCT ACC ACG        451
Asp Ser Ser Asp Gly Ser Leu Glu Asp Asp Asp Tyr His Ala Thr Thr
                105                 110                 115

GAA ACA ATC ATT ACC ATG CCT ACA GAG TCT GAC TTT CTA ATG CAA GCG        499
Glu Thr Ile Ile Thr Met Pro Thr Glu Ser Asp Phe Leu Met Gln Ala
            120                 125                 130

GAT GGC AAG CCC AAA TGT TGC TTT TTT AAA TTT AGC TCT AAA ATA CAG        547
Asp Gly Lys Pro Lys Cys Cys Phe Phe Lys Phe Ser Ser Lys Ile Gln
        135                 140                 145

TAC AAC AAA GTA GTA AAA GCC CAA CTG TGG ATA TAT CTC AGA CCC GTC        595
Tyr Asn Lys Val Val Lys Ala Gln Leu Trp Ile Tyr Leu Arg Pro Val
    150                 155                 160

AAG ACT CCT ACA ACA GTG TTT GTG CAA ATC CTG AGA CTC ATC AAA CCC        643
Lys Thr Pro Thr Thr Val Phe Val Gln Ile Leu Arg Leu Ile Lys Pro
165                 170                 175                 180

ATG AAA GAC GGT ACA AGG TAT ACT GGA ATC CGA TCT CTG AAA CTT GAC        691
Met Lys Asp Gly Thr Arg Tyr Thr Gly Ile Arg Ser Leu Lys Leu Asp
                185                 190                 195

ATG AGC CCA GGC ACT GGT ATT TGG CAG AGT ATT GAT GTG AAG ACA GTG        739
Met Ser Pro Gly Thr Gly Ile Trp Gln Ser Ile Asp Val Lys Thr Val
            200                 205                 210

TTG CAA AAT TGG CTC AAA CAG CCT GAA TCC AAC TTA GGC ATT GAA ATC        787
Leu Gln Asn Trp Leu Lys Gln Pro Glu Ser Asn Leu Gly Ile Glu Ile
        215                 220                 225

AAA GCT TTG GAT GAG AAT GGC CAT GAT CTT GCT GTA ACC TTC CCA GGA        835
Lys Ala Leu Asp Glu Asn Gly His Asp Leu Ala Val Thr Phe Pro Gly
    230                 235                 240

CCA GGA GAA GAT GGG CTG AAT CCC TTT TTA GAA GTC AAG GTG ACA GAC        883
Pro Gly Glu Asp Gly Leu Asn Pro Phe Leu Glu Val Lys Val Thr Asp
245                 250                 255                 260

ACA CCC AAG AGG TCC CGG AGA GAC TTT GGG CTT GAC TGC GAT GAG CAC        931
Thr Pro Lys Arg Ser Arg Arg Asp Phe Gly Leu Asp Cys Asp Glu His
```

```
                  265                              270                             275
TCC  ACG  GAA  TCC  CGG  TGC  TGC  CGC  TAC  CCC  CTC  ACG  GTC  GAT  TTT  GAA         979
Ser  Thr  Glu  Ser  Arg  Cys  Cys  Arg  Tyr  Pro  Leu  Thr  Val  Asp  Phe  Glu
               280                         285                    290

GCC  TTT  GGA  TGG  GAC  TGG  ATT  ATC  GCA  CCC  AAA  AGA  TAT  AAG  GCC  AAT         1027
Ala  Phe  Gly  Trp  Asp  Trp  Ile  Ile  Ala  Pro  Lys  Arg  Tyr  Lys  Ala  Asn
          295                         300                    305

TAC  TGC  TCA  GGA  GAG  TGT  GAA  TTT  GTG  TTT  TTA  CAA  AAA  TAT  CCG  CAT         1075
Tyr  Cys  Ser  Gly  Glu  Cys  Glu  Phe  Val  Phe  Leu  Gln  Lys  Tyr  Pro  His
     310                         315                    320

ACT  CAT  CTT  GTG  CAC  CAA  GCA  AAC  CCC  AGA  GGC  TCA  GCA  GGC  CCT  TGC         1123
Thr  His  Leu  Val  His  Gln  Ala  Asn  Pro  Arg  Gly  Ser  Ala  Gly  Pro  Cys
325                    330                         335                         340

TGC  ACT  CCG  ACA  AAA  ATG  TCT  CCC  ATT  AAT  ATG  CTA  TAT  TTT  AAT  GGC         1171
Cys  Thr  Pro  Thr  Lys  Met  Ser  Pro  Ile  Asn  Met  Leu  Tyr  Phe  Asn  Gly
                    345                         350                         355

AAA  GAA  CAA  ATA  ATA  TAT  GGG  AAA  ATT  CCA  GCC  ATG  GTA  GTA  GAC  CGC         1219
Lys  Glu  Gln  Ile  Ile  Tyr  Gly  Lys  Ile  Pro  Ala  Met  Val  Val  Asp  Arg
               360                         365                    370

TGT  GGG  TGC  TCA  TGAGCTTGC  ATTAGGTTAG  AAACTTCCCA  AGTCATGGAA  GGTCT            1276
Cys  Gly  Cys  Ser
               375

TCCCCTCAAT  TTCGAAACTG  TGAATTCAAG  CACCACAGGC  TGTAGGCCTT  GAGTATGCTC              1336

TAGTAACGTA  AGCACAAGCT  ACAGTGTATG  AACTAAAAGA  GAGAATAGAT  GCAATGGTTG              1396

GCATTCAACC  ACCAAAATAA  ACCATACTAT  AGGATGTTGT  ATGATTTCCA  GAGTTTTTGA              1456

AATAGATGGA  GATCAAATTA  CATTTATGTC  CATATATGTA  TATTACAACT  ACAATCTAGG              1516

CAAGGAAGTG  AGAGCACATC  TTGTGGTCTG  CTGAGTTAGG  AGGGTATGAT  TAAAAGGTAA              1576

AGTCTTATTT  CCTAACAGTT  TCACTTAATA  TTTACAGAAG  AATCTATATG  TAGCCTTTGT              1636

AAAGTGTAGG  ATTGTTATCA  TTTAAAAACA  TCATGTACAC  TTATATTTGT  ATTGTATACT              1696

TGGTAAGATA  AAATTCCACA  AGTAGGAAT   GGGGCCTCAC  ATACACATTG  CCATTCCTAT              1756

TATAATTGGA  CAATCCACCA  CGGTGCTAAT  GCAGTGCTGA  ATGGCTCCTA  CTGGACCTCT              1816

CGATAGAACA  CTCTACAAAG  TACGAGTCTC  TCTCTCCCTT  CCAGGTGCAT  CTCCACACAC              1876

ACAGCACTAA  GTGTTCAATG  CATTTTCTTT  AAGGAAAGAA  GAATCTTTTT  TTCTAGAGGT              1936

CAACTTTCAG  TCAACTCTAG  CACAGCGGGA  GTGACTGCTG  CATCTTAAAA  GGCAGCCAAA              1996

CAGTATTCAT  TTTTTAATCT  AAATTTCAAA  ATCACTGTCT  GCCTTATCA   CATGGCAATT              2056

TTGTGGTAAA  ATAATGGAAA  TGACTGGTTC  TATCAATATT  GTATAAAAGA  CTCTGAAACA              2116

ATTACATTTA  TATAATATGT  ATACAATATT  GTTTTGTAAA  TAAGTGTCTC  CTTTTATATT              2176

TACTTTGGTA  TATTTTTACA  CTAATGAAAT  TTCAAATCAT  TAAAGTACAA  AGACATGTCA              2236

TGTATCACAA  AAAAGGTGAC  TGCTTCTATT  TCAGAGTGAA  TTAGCAGATT  CAATAGTGGT              2296

CTTAAAACTC  TGTATGTTAA  GATTAGAAGG  TTATATTACA  ATCAATTTAT  GTATTTTTA               2356

CATTATCAAC  TTATGGTTTC  ATGGTGGCTG  TATCTATGAA  TGTGGCTCCC  AGTCAAATTT              2416

CAATGCCCCA  CCATTTTAAA  AATTACAAGC  ATTACTAAAC  ATACCAACAT  GTATCTAAAG              2476

AAATACAAAT  ATGGTATCTC  AATAACAGCT  ACTTTTTTAT  TTTATAATTT  GACAATGAAT              2536

ACATTTCTTT  TATTTACTTC  AGTTTTATAA  ATTGGAACTT  TGTTTATCAA  ATGTATTGTA              2596

CTCATAGCTA  AATGAAATTA  TTTCTTACAT  AAAAATGTGT  AGAAACTATA  AATTAAAGTG              2656

TTTTCACATT  TTTGAAAGGC                                                              2676
```

( 2 ) INFORMATION FOR SEQ ID NO:12:

( i ) SEQUENCE CHARACTERISTICS:
    ( A ) LENGTH: 376 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:12:

```
Met Met Gln Lys Leu Gln Met Tyr Val Tyr Ile Tyr Leu Phe Met Leu
 1               5                  10                  15
Ile Ala Ala Gly Pro Val Asp Leu Asn Glu Gly Ser Glu Arg Glu Glu
                 20                  25                  30
Asn Val Glu Lys Glu Gly Leu Cys Asn Ala Cys Ala Trp Arg Gln Asn
             35                  40                  45
Thr Arg Tyr Ser Arg Ile Glu Ala Ile Lys Ile Gln Ile Leu Ser Lys
         50                  55                  60
Leu Arg Leu Glu Thr Ala Pro Asn Ile Ser Lys Asp Ala Ile Arg Gln
 65                  70                  75                  80
Leu Leu Pro Arg Ala Pro Pro Leu Arg Glu Leu Ile Asp Gln Tyr Asp
                 85                  90                  95
Val Gln Arg Asp Asp Ser Ser Asp Gly Ser Leu Glu Asp Asp Asp Tyr
                100                 105                 110
His Ala Thr Thr Glu Thr Ile Ile Thr Met Pro Thr Glu Ser Asp Phe
             115                 120                 125
Leu Met Gln Ala Asp Gly Lys Pro Lys Cys Cys Phe Phe Lys Phe Ser
        130                 135                 140
Ser Lys Ile Gln Tyr Asn Lys Val Val Lys Ala Gln Leu Trp Ile Tyr
145                 150                 155                 160
Leu Arg Pro Val Lys Thr Pro Thr Thr Val Phe Val Gln Ile Leu Arg
                165                 170                 175
Leu Ile Lys Pro Met Lys Asp Gly Thr Arg Tyr Thr Gly Ile Arg Ser
                180                 185                 190
Leu Lys Leu Asp Met Ser Pro Gly Thr Gly Ile Trp Gln Ser Ile Asp
            195                 200                 205
Val Lys Thr Val Leu Gln Asn Trp Leu Lys Gln Pro Glu Ser Asn Leu
    210                 215                 220
Gly Ile Glu Ile Lys Ala Leu Asp Glu Asn Gly His Asp Leu Ala Val
225                 230                 235                 240
Thr Phe Pro Gly Pro Gly Glu Asp Gly Leu Asn Pro Phe Leu Glu Val
                245                 250                 255
Lys Val Thr Asp Thr Pro Lys Arg Ser Arg Arg Asp Phe Gly Leu Asp
            260                 265                 270
Cys Asp Glu His Ser Thr Glu Ser Arg Cys Cys Arg Tyr Pro Leu Thr
        275                 280                 285
Val Asp Phe Glu Ala Phe Gly Trp Asp Trp Ile Ile Ala Pro Lys Arg
    290                 295                 300
Tyr Lys Ala Asn Tyr Cys Ser Gly Glu Cys Glu Phe Val Phe Leu Gln
305                 310                 315                 320
Lys Tyr Pro His Thr His Leu Val His Gln Ala Asn Pro Arg Gly Ser
                325                 330                 335
Ala Gly Pro Cys Cys Thr Pro Thr Lys Met Ser Pro Ile Asn Met Leu
            340                 345                 350
Tyr Phe Asn Gly Lys Glu Gln Ile Ile Tyr Gly Lys Ile Pro Ala Met
        355                 360                 365
```

```
Val  Val  Asp  Arg  Cys  Gly  Cys  Ser
     370                 375
```

( 2 ) INFORMATION FOR SEQ ID NO:13:

( i ) SEQUENCE CHARACTERISTICS:
        ( A ) LENGTH: 2743 base pairs
        ( B ) TYPE: nucleic acid
        ( C ) STRANDEDNESS: single
        ( D ) TOPOLOGY: linear ( i i ) MOLECULE TYPE: Genomic DNA ( v i i ) IMMEDIATE SOURCE:
        ( B ) CLONE: Human GDF-8

( i x ) FEATURE:
        ( A ) NAME/KEY: CDS
        ( B ) LOCATION: 59...1183

( x i ) SEQUENCE DESCRIPTION: SEQ ID NO:13:

```
AAGAAAAGTA  AAAGGAAGAA  ACAAGAACAA  GAAAAAAGAT  TATATTGATT  TTAAAATC                 58

ATG  CAA  AAA  CTG  CAA  CTC  TGT  GTT  TAT  ATT  TAC  CTG  TTT  ATG  CTG  ATT       106
Met  Gln  Lys  Leu  Gln  Leu  Cys  Val  Tyr  Ile  Tyr  Leu  Phe  Met  Leu  Ile
 1                  5                        10                       15

GTT  GCT  GGT  CCA  GTG  GAT  CTA  AAT  GAG  AAC  AGT  GAG  CAA  AAA  GAA  AAT       154
Val  Ala  Gly  Pro  Val  Asp  Leu  Asn  Glu  Asn  Ser  Glu  Gln  Lys  Glu  Asn
               20                       25                       30

GTG  GAA  AAA  GAG  GGG  CTG  TGT  AAT  GCA  TGT  ACT  TGG  AGA  CAA  AAC  ACT       202
Val  Glu  Lys  Glu  Gly  Leu  Cys  Asn  Ala  Cys  Thr  Trp  Arg  Gln  Asn  Thr
          35                       40                       45

AAA  TCT  TCA  AGA  ATA  GAA  GCC  ATT  AAG  ATA  CAA  ATC  CTC  AGT  AAA  CTT       250
Lys  Ser  Ser  Arg  Ile  Glu  Ala  Ile  Lys  Ile  Gln  Ile  Leu  Ser  Lys  Leu
     50                       55                       60

CGT  CTG  GAA  ACA  GCT  CCT  AAC  ATC  AGC  AAA  GAT  GTT  ATA  AGA  CAA  CTT       298
Arg  Leu  Glu  Thr  Ala  Pro  Asn  Ile  Ser  Lys  Asp  Val  Ile  Arg  Gln  Leu
65                       70                       75                       80

TTA  CCC  AAA  GCT  CCT  CCA  CTC  CGG  GAA  CTG  ATT  GAT  CAG  TAT  GAT  GTC       346
Leu  Pro  Lys  Ala  Pro  Pro  Leu  Arg  Glu  Leu  Ile  Asp  Gln  Tyr  Asp  Val
                    85                       90                       95

CAG  AGG  GAT  GAC  AGC  AGC  GAT  GGC  TCT  TTG  GAA  GAT  GAC  GAT  TAT  CAC       394
Gln  Arg  Asp  Asp  Ser  Ser  Asp  Gly  Ser  Leu  Glu  Asp  Asp  Asp  Tyr  His
               100                      105                      110

GCT  ACA  ACG  GAA  ACA  ATC  ATT  ACC  ATG  CCT  ACA  GAG  TCT  GAT  TTT  CTA       442
Ala  Thr  Thr  Glu  Thr  Ile  Ile  Thr  Met  Pro  Thr  Glu  Ser  Asp  Phe  Leu
          115                      120                      125

ATG  CAA  GTG  GAT  GGA  AAA  CCC  AAA  TGT  TGC  TTC  TTT  AAA  TTT  AGC  TCT       490
Met  Gln  Val  Asp  Gly  Lys  Pro  Lys  Cys  Cys  Phe  Phe  Lys  Phe  Ser  Ser
     130                      135                      140

AAA  ATA  CAA  TAC  AAT  AAA  GTA  GTA  AAG  GCC  CAA  CTA  TGG  ATA  TAT  TTG       538
Lys  Ile  Gln  Tyr  Asn  Lys  Val  Val  Lys  Ala  Gln  Leu  Trp  Ile  Tyr  Leu
145                      150                      155                      160

AGA  CCC  GTC  GAG  ACT  CCT  ACA  ACA  GTG  TTT  GTG  CAA  ATC  CTG  AGA  CTC       586
Arg  Pro  Val  Glu  Thr  Pro  Thr  Thr  Val  Phe  Val  Gln  Ile  Leu  Arg  Leu
                    165                      170                      175

ATC  AAA  CCT  ATG  AAA  GAC  GGT  ACA  AGG  TAT  ACT  GGA  ATC  CGA  TCT  CTG       634
Ile  Lys  Pro  Met  Lys  Asp  Gly  Thr  Arg  Tyr  Thr  Gly  Ile  Arg  Ser  Leu
               180                      185                      190

AAA  CTT  GAC  ATG  AAC  CCA  GGC  ACT  GGT  ATT  TGG  CAG  AGC  ATT  GAT  GTG       682
Lys  Leu  Asp  Met  Asn  Pro  Gly  Thr  Gly  Ile  Trp  Gln  Ser  Ile  Asp  Val
          195                      200                      205

AAG  ACA  GTG  TTG  CAA  AAT  TGG  CTC  AAA  CAA  CCT  GAA  TCC  AAC  TTA  GGC       730
Lys  Thr  Val  Leu  Gln  Asn  Trp  Leu  Lys  Gln  Pro  Glu  Ser  Asn  Leu  Gly
```

-continued

```
                210                         215                         220
ATT GAA ATA AAA GCT TTA GAT GAG AAT GGT CAT GAT CTT GCT GTA ACC        778
Ile Glu Ile Lys Ala Leu Asp Glu Asn Gly His Asp Leu Ala Val Thr
225             230                     235                     240

TTC CCA GGA CCA GGA GAA GAT GGG CTG AAT CCG TTT TTA GAG GTC AAG        826
Phe Pro Gly Pro Gly Glu Asp Gly Leu Asn Pro Phe Leu Glu Val Lys
                245                     250                     255

GTA ACA GAC ACA CCA AAA AGA TCC AGA AGG GAT TTT GGT CTT GAC TGT        874
Val Thr Asp Thr Pro Lys Arg Ser Arg Arg Asp Phe Gly Leu Asp Cys
                260                     265                     270

GAT GAG CAC TCA ACA GAA TCA CGA TGC TGT CGT TAC CCT CTA ACT GTG        922
Asp Glu His Ser Thr Glu Ser Arg Cys Cys Arg Tyr Pro Leu Thr Val
            275                     280                     285

GAT TTT GAA GCT TTT GGA TGG GAT TGG ATT ATC GCT CCT AAA AGA TAT        970
Asp Phe Glu Ala Phe Gly Trp Asp Trp Ile Ile Ala Pro Lys Arg Tyr
290                     295                     300

AAG GCC AAT TAC TGC TCT GGA GAG TGT GAA TTT GTA TTT TTA CAA AAA       1018
Lys Ala Asn Tyr Cys Ser Gly Glu Cys Glu Phe Val Phe Leu Gln Lys
305                     310                     315                 320

TAT CCT CAT ACT CAT CTG GTA CAC CAA GCA AAC CCC AGA GGT TCA GCA       1066
Tyr Pro His Thr His Leu Val His Gln Ala Asn Pro Arg Gly Ser Ala
                        325                     330                 335

GGC CCT TGC TGT ACT CCC ACA AAG ATG TCT CCA ATT AAT ATG CTA TAT       1114
Gly Pro Cys Cys Thr Pro Thr Lys Met Ser Pro Ile Asn Met Leu Tyr
                340                     345                     350

TTT AAT GGC AAA GAA CAA ATA ATA TAT GGG AAA ATT CCA GCG ATG GTA       1162
Phe Asn Gly Lys Glu Gln Ile Ile Tyr Gly Lys Ile Pro Ala Met Val
                355                     360                     365

GTA GAC CGC TGT GGG TGC TCA TGAGATTTAT ATTAAGCGTT CATAACTTCC TAAAAC   1219
Val Asp Arg Cys Gly Cys Ser
                370         375

ATGGAAGGTT TTCCCCTCAA CAATTTTGAA GCTGTGAAAT TAAGTACCAC AGGCTATAGG   1279

CCTAGAGTAT GCTACAGTCA CTTAAGCATA AGCTACAGTA TGTAAACTAA AAGGGGGAAT   1339

ATATGCAATG GTTGGCATTT AACCATCCAA ACAAATCATA CAAGAAAGTT TATGATTTC    1399

CAGAGTTTTT GAGCTAGAAG GAGATCAAAT TACATTTATG TTCCTATATA TTACAACATC   1459

GGCGAGGAAA TGAAAGCGAT TCTCCTTGAG TTCTGATGAA TTAAAGGAGT ATGCTTTAAA   1519

GTCTATTTCT TTAAAGTTTT GTTTAATATT TACAGAAAAA TCCACATACA GTATTGGTAA   1579

AATGCAGGAT TGTTATATAC CATCATTCGA ATCATCCTTA AACACTTGAA TTTATATTGT   1639

ATGGTAGTAT ACTTGGTAAG ATAAAATTCC ACAAAATAG GGATGGTGCA GCATATGCAA    1699

TTTCCATTCC TATTATAATT GACACAGTAC ATTAACAATC CATGCCAACG GTGCTAATAC   1759

GATAGGCTGA ATGTCTGAGG CTACCAGGTT TATCACATAA AAAACATTCA GTAAATAGT    1819

AAGTTTCTCT TTTCTTCAGG TGCATTTTCC TACACCTCCA ATGAGGAAT GGATTTTCTT    1879

TAATGTAAGA AGAATCATTT TTCTAGAGGT TGGCTTTCAA TTCTGTAGCA TACTTGGAGA   1939

AACTGCATTA TCTTAAAAGG CAGTCAAATG GTGTTTGTTT TATCAAAAT GTCAAAATAA    1999

CATACTTGGA GAAGTATGTA ATTTTGTCTT TGGAAAATTA CAACACTGCC TTTGCAACAC   2059

TGCAGTTTTT ATGGTAAAAT AATAGAAATG ATCGACTCTA TCAATATTGT ATAAAAAGAC   2119

TGAAACAATG CATTTATATA ATATGTATAC AATATTGTTT TGTAAATAAG GTCTCCTTT    2179

TTTATTTACT TTGGTATATT TTTACACTAA GGACATTTCA AATTAAGTAC TAAGGCACAA   2239

AGACATGTCA TGCATCACAG AAAAGCAACT ACTTATATTT CAGAGCAAAT TAGCAGATTA   2299

AATAGTGGTC TTAAAACTCC ATATGTTAAT GATTAGATGG TTATATTACA ATCATTTTAT   2359
```

```
ATTTTTTTAC ATGATTAACA TTCACTTATG GATTCATGAT GGCTGTATAA AGTGAATTTG      2419

AAATTTCAAT GGTTTACTGT CATTGTGTTT AAATCTCAAC GTTCCATTAT TTTAATACTT      2479

GCAAAAACAT TACTAAGTAT ACCAAAATAA TTGACTCTAT TATCTGAAAT GAAGAATAAA      2539

CTGATGCTAT CTCAACAATA ACTGTTACTT TTATTTTATA ATTTGATAAT GAATATATTT      2599

CTGCATTTAT TTACTTCTGT TTTGTAAATT GGGATTTTGT TAATCAAATT TATTGTACTA      2659

TGACTAAATG AAATTATTTC TTACATCTAA TTTGTAGAAA CAGTATAAGT TATATTAAAG      2719

TGTTTTCACA TTTTTTTGAA AGAC                                            2743
```

( 2 ) INFORMATION FOR SEQ ID NO:14:

( i ) SEQUENCE CHARACTERISTICS:
        ( A ) LENGTH: 375 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:14:

```
Met Gln Lys Leu Gln Leu Cys Val Tyr Ile Tyr Leu Phe Met Leu Ile
 1               5                  10                  15

Val Ala Gly Pro Val Asp Leu Asn Glu Asn Ser Glu Gln Lys Glu Asn
                20                  25                  30

Val Glu Lys Glu Gly Leu Cys Asn Ala Cys Thr Trp Arg Gln Asn Thr
                35                  40                  45

Lys Ser Ser Arg Ile Glu Ala Ile Lys Ile Gln Ile Leu Ser Lys Leu
            50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                    85                  90                  95

Gln Arg Asp Asp Ser Ser Asp Gly Ser Leu Glu Asp Asp Asp Tyr His
               100                 105                 110

Ala Thr Thr Glu Thr Ile Ile Thr Met Pro Thr Glu Ser Asp Phe Leu
               115                 120                 125

Met Gln Val Asp Gly Lys Pro Lys Cys Cys Phe Phe Lys Phe Ser Ser
       130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                    165                 170                 175

Ile Lys Pro Met Lys Asp Gly Thr Arg Tyr Thr Gly Ile Arg Ser Leu
               180                 185                 190

Lys Leu Asp Met Asn Pro Gly Thr Gly Ile Trp Gln Ser Ile Asp Val
           195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                    245                 250                 255

Val Thr Asp Thr Pro Lys Arg Ser Arg Arg Asp Phe Gly Leu Asp Cys
               260                 265                 270

Asp Glu His Ser Thr Glu Ser Arg Cys Cys Arg Tyr Pro Leu Thr Val
```

|     | 275 |     |     |     |     | 280 |     |     |     |     | 285 |     |     |     |
|-----|-----|-----|-----|-----|-----|-----|-----|-----|-----|-----|-----|-----|-----|-----|
| Asp | Phe | Glu | Ala | Phe | Gly | Trp | Asp | Trp | Ile | Ile | Ala | Pro | Lys | Arg | Tyr |
|     | 290 |     |     |     |     | 295 |     |     |     |     | 300 |     |     |     |
| Lys | Ala | Asn | Tyr | Cys | Ser | Gly | Glu | Cys | Glu | Phe | Val | Phe | Leu | Gln | Lys |
| 305 |     |     |     |     | 310 |     |     |     |     | 315 |     |     |     |     | 320 |
| Tyr | Pro | His | Thr | His | Leu | Val | His | Gln | Ala | Asn | Pro | Arg | Gly | Ser | Ala |
|     |     |     |     | 325 |     |     |     |     | 330 |     |     |     |     | 335 |     |
| Gly | Pro | Cys | Cys | Thr | Pro | Thr | Lys | Met | Ser | Pro | Ile | Asn | Met | Leu | Tyr |
|     |     |     | 340 |     |     |     |     | 345 |     |     |     |     | 350 |     |     |
| Phe | Asn | Gly | Lys | Glu | Gln | Ile | Ile | Tyr | Gly | Lys | Ile | Pro | Ala | Met | Val |
|     |     | 355 |     |     |     |     | 360 |     |     |     |     | 365 |     |     |     |
| Val | Asp | Arg | Cys | Gly | Cys | Ser |
|     | 370 |     |     |     |     | 375 |

( 2 ) INFORMATION FOR SEQ ID NO:15:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: Genomic DNA ( v i i ) IMMEDIATE SOURCE:
        ( B ) CLONE: #83

( i x ) FEATURE:
        ( A ) NAME/KEY: CDS
        ( B ) LOCATION: 1..34

( x i ) SEQUENCE DESCRIPTION: SEQ ID NO:15:

CGCGGATCCG TGGATCTAAA TGAGAACAGT GAGC 34

( 2 ) INFORMATION FOR SEQ ID NO:16:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Genomic DNA ( v i i ) IMMEDIATE SOURCE:
        ( B ) CLONE: #84

( i x ) FEATURE:
        ( A ) NAME/KEY: CDS
        ( B ) LOCATION: 1..37

( x i ) SEQUENCE DESCRIPTION: SEQ ID NO:16:

CGCGAATTCT CAGGTAATGA TTGTTTCCGT TGTAGCG 37

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Genomic DNA ( v i i ) IMMEDIATE SOURCE:
        ( B ) CLONE: #100

( i x ) FEATURE:
        ( A ) NAME/KEY: CDS (B) LOCATION: 1..20

(x i) SEQUENCE DESCRIPTION: SEQ ID NO:17:

ACACTAAATC TTCAAGAATA 20

(2) INFORMATION FOR SEQ ID NO:18:

(i) SEQUENCE CHARACTERISTICS:
        (A) LENGTH: 123 amino acids
        (B) TYPE: amino acid
        (D) TOPOLOGY: linear (i i) MOLECULE TYPE: protein (v i i) IMMEDIATE SOURCE:
        (B) CLONE: GDF-1

(i x) FEATURE:
        (A) NAME/KEY: Protein
        (B) LOCATION: 1..123

(x i) SEQUENCE DESCRIPTION: SEQ ID NO:18:

```
Arg Pro Arg Arg Asp Ala Glu Pro Val Leu Gly Gly Gly Pro Gly Gly
 1               5                  10                  15
Ala Cys Arg Ala Arg Arg Leu Tyr Val Ser Phe Arg Glu Val Gly Trp
                20                  25                  30
His Arg Trp Val Ile Ala Pro Arg Gly Phe Leu Ala Asn Tyr Cys Gln
            35                  40                  45
Gly Gln Cys Ala Leu Pro Val Ala Leu Ser Gly Ser Gly Gly Pro Pro
        50                  55                  60
Ala Leu Asn His Ala Val Leu Arg Ala Leu Met His Ala Ala Ala Pro
65                  70                  75                  80
Gly Ala Ala Asp Leu Pro Cys Cys Val Pro Ala Arg Leu Ser Pro Ile
                85                  90                  95
Ser Val Leu Phe Phe Asp Asn Ser Asp Asn Val Val Leu Arg Gln Tyr
                100                 105                 110
Glu Asp Met Val Val Asp Glu Cys Gly Cys Arg
                115                 120
```

(2) INFORMATION FOR SEQ ID NO:19:

(i) SEQUENCE CHARACTERISTICS:
        (A) LENGTH: 118 amino acids
        (B) TYPE: amino acid
        (D) TOPOLOGY: linear (i i) MOLECULE TYPE: protein (v i i) IMMEDIATE SOURCE:
        (B) CLONE: BMP-2

(i x) FEATURE:
        (A) NAME/KEY: Protein
        (B) LOCATION: 1..118

(x i) SEQUENCE DESCRIPTION: SEQ ID NO:19:

```
Arg Glu Lys Arg Gln Ala Lys His Lys Gln Arg Lys Arg Leu Lys Ser
 1               5                  10                  15
Ser Cys Lys Arg His Pro Leu Tyr Val Asp Phe Ser Asp Val Gly Trp
                20                  25                  30
Asn Asp Trp Ile Val Ala Pro Pro Gly Tyr His Ala Phe Tyr Cys His
            35                  40                  45
Gly Glu Cys Pro Phe Pro Leu Ala Asp His Leu Asn Ser Thr Asn His
        50                  55                  60
```

```
Ala  Ile  Val  Gln  Thr  Leu  Val  Asn  Ser  Val  Asn  Ser  Lys  Ile  Pro  Lys
 65                  70                      75                           80

Ala  Cys  Cys  Val  Pro  Thr  Glu  Leu  Ser  Ala  Ile  Ser  Met  Leu  Tyr  Leu
                     85                      90                       95

Asp  Glu  Asn  Glu  Lys  Val  Val  Leu  Lys  Asn  Tyr  Gln  Asp  Met  Val  Val
               100                      105                      110

Glu  Gly  Cys  Gly  Cys  Arg
               115
```

(2) INFORMATION FOR SEQ ID NO:20:

(i) SEQUENCE CHARACTERISTICS:
        (A) LENGTH: 118 amino acids
        (B) TYPE: amino acid
        (D) TOPOLOGY: linear (ii) MOLECULE TYPE: protein (vii) IMMEDIATE SOURCE:
        (B) CLONE: BMP-4

(ix) FEATURE:
        (A) NAME/KEY: Protein
        (B) LOCATION: 1..118

(xi) SEQUENCE DESCRIPTION: SEQ ID NO:20:

```
Lys  Arg  Ser  Pro  Lys  His  His  Ser  Gln  Arg  Ala  Arg  Lys  Lys  Asn  Lys
  1                  5                       10                          15

Asn  Cys  Arg  Arg  His  Ser  Leu  Tyr  Val  Asp  Phe  Ser  Asp  Val  Gly  Trp
                20                      25                       30

Asn  Asp  Trp  Ile  Val  Ala  Pro  Pro  Gly  Tyr  Gln  Ala  Phe  Tyr  Cys  His
                35                      40                       45

Gly  Asp  Cys  Pro  Phe  Pro  Leu  Ala  Asp  His  Leu  Asn  Ser  Thr  Asn  His
           50                      55                       60

Ala  Ile  Val  Gln  Thr  Leu  Val  Asn  Ser  Val  Asn  Ser  Ser  Ile  Pro  Lys
 65                  70                      75                           80

Ala  Cys  Cys  Val  Pro  Thr  Glu  Leu  Ser  Ala  Ile  Ser  Met  Leu  Tyr  Leu
                     85                      90                       95

Asp  Glu  Tyr  Asp  Lys  Val  Val  Leu  Lys  Asn  Tyr  Gln  Glu  Met  Val  Val
               100                      105                      110

Glu  Gly  Cys  Gly  Cys  Arg
               115
```

(2) INFORMATION FOR SEQ ID NO:21:

(i) SEQUENCE CHARACTERISTICS:
        (A) LENGTH: 119 amino acids
        (B) TYPE: amino acid
        (D) TOPOLOGY: linear (ii) MOLECULE TYPE: protein (vii) IMMEDIATE SOURCE:
        (B) CLONE: Vgr-1

(ix) FEATURE:
        (A) NAME/KEY: Protein
        (B) LOCATION: 1..119

(xi) SEQUENCE DESCRIPTION: SEQ ID NO:21:

```
Ser  Arg  Gly  Ser  Gly  Ser  Ser  Asp  Tyr  Asn  Gly  Ser  Glu  Leu  Lys  Thr
  1                  5                       10                          15

Ala  Cys  Lys  Lys  His  Glu  Leu  Tyr  Val  Ser  Phe  Gln  Asp  Leu  Gly  Trp
                20                      25                       30
```

```
Gln  Asp  Trp  Ile  Ile  Ala  Pro  Lys  Gly  Tyr  Ala  Ala  Asn  Tyr  Cys  Asp
          35                      40                      45

Gly  Glu  Cys  Ser  Phe  Pro  Leu  Asn  Ala  His  Met  Asn  Ala  Thr  Asn  His
     50                       55                      60

Ala  Ile  Val  Gln  Thr  Leu  Val  His  Leu  Met  Asn  Pro  Glu  Tyr  Val  Pro
65                       70                      75                           80

Lys  Pro  Cys  Cys  Ala  Pro  Thr  Lys  Leu  Asn  Ala  Ile  Ser  Val  Leu  Tyr
               85                           90                           95

Phe  Asp  Asp  Asn  Ser  Asn  Val  Ile  Leu  Lys  Lys  Tyr  Arg  Asn  Met  Val
               100                      105                     110

Val  Arg  Ala  Cys  Gly  Cys  His
               115
```

(2) INFORMATION FOR SEQ ID NO:22:

(i) SEQUENCE CHARACTERISTICS:
        (A) LENGTH: 119 amino acids
        (B) TYPE: amino acid
        (D) TOPOLOGY: linear (ii) MOLECULE TYPE: protein (vii) IMMEDIATE SOURCE:
        (B) CLONE: OP-1

(ix) FEATURE:
        (A) NAME/KEY: Protein
        (B) LOCATION: 1..119

(xi) SEQUENCE DESCRIPTION: SEQ ID NO:22:

```
Leu  Arg  Met  Ala  Asn  Val  Ala  Glu  Asn  Ser  Ser  Asp  Gln  Arg  Gln
1                   5                        10                      15

Ala  Cys  Lys  Lys  His  Glu  Leu  Tyr  Val  Ser  Phe  Arg  Asp  Leu  Gly  Trp
               20                       25                      30

Gln  Asp  Trp  Ile  Ile  Ala  Pro  Glu  Gly  Tyr  Ala  Ala  Tyr  Tyr  Cys  Glu
          35                      40                      45

Gly  Glu  Cys  Ala  Phe  Pro  Leu  Asn  Ser  Tyr  Met  Asn  Ala  Thr  Asn  His
     50                       55                      60

Ala  Ile  Val  Gln  Thr  Leu  Val  His  Phe  Ile  Asn  Pro  Glu  Thr  Val  Pro
65                       70                      75                           80

Lys  Pro  Cys  Cys  Ala  Pro  Thr  Gln  Leu  Asn  Ala  Ile  Ser  Val  Leu  Tyr
               85                           90                           95

Phe  Asp  Asp  Ser  Ser  Asn  Val  Ile  Leu  Lys  Lys  Tyr  Arg  Asn  Met  Val
               100                      105                     110

Val  Arg  Ala  Cys  Gly  Cys  His
               115
```

(2) INFORMATION FOR SEQ ID NO:23:

(i) SEQUENCE CHARACTERISTICS:
        (A) LENGTH: 119 amino acids
        (B) TYPE: amino acid
        (D) TOPOLOGY: linear (ii) MOLECULE TYPE: protein (vii) IMMEDIATE SOURCE:
        (B) CLONE: BMP-5

(ix) FEATURE:
        (A) NAME/KEY: Protein
        (B) LOCATION: 1..119

(xi) SEQUENCE DESCRIPTION: SEQ ID NO:23:

| Ser | Arg | Met | Ser | Ser | Val | Gly | Asp | Tyr | Asn | Thr | Ser | Glu | Gln | Lys | Gln |
|---|---|---|---|---|---|---|---|---|---|---|---|---|---|---|---|
| 1 | | | | 5 | | | | | 10 | | | | | 15 | |

| Ala | Cys | Lys | Lys | His | Glu | Leu | Tyr | Val | Ser | Phe | Arg | Asp | Leu | Gly | Trp |
|---|---|---|---|---|---|---|---|---|---|---|---|---|---|---|---|
| | | | 20 | | | | | 25 | | | | | 30 | | |

| Gln | Asp | Trp | Ile | Ile | Ala | Pro | Glu | Gly | Tyr | Ala | Ala | Phe | Tyr | Cys | Asp |
|---|---|---|---|---|---|---|---|---|---|---|---|---|---|---|---|
| | | 35 | | | | | 40 | | | | | 45 | | | |

| Gly | Glu | Cys | Ser | Phe | Pro | Leu | Asn | Ala | His | Met | Asn | Ala | Thr | Asn | His |
|---|---|---|---|---|---|---|---|---|---|---|---|---|---|---|---|
| | 50 | | | | | 55 | | | | | 60 | | | | |

| Ala | Ile | Val | Gln | Thr | Leu | Val | His | Leu | Met | Phe | Pro | Asp | His | Val | Pro |
|---|---|---|---|---|---|---|---|---|---|---|---|---|---|---|---|
| 65 | | | | | 70 | | | | | 75 | | | | | 80 |

| Lys | Pro | Cys | Cys | Ala | Pro | Thr | Lys | Leu | Asn | Ala | Ile | Ser | Val | Leu | Tyr |
|---|---|---|---|---|---|---|---|---|---|---|---|---|---|---|---|
| | | | | 85 | | | | | 90 | | | | | 95 | |

| Phe | Asp | Asp | Ser | Ser | Asn | Val | Ile | Leu | Lys | Lys | Tyr | Arg | Asn | Met | Val |
|---|---|---|---|---|---|---|---|---|---|---|---|---|---|---|---|
| | | | 100 | | | | | 105 | | | | | 110 | | |

| Val | Arg | Ser | Cys | Gly | Cys | His |
|---|---|---|---|---|---|---|
| | | 115 | | | | |

( 2 ) INFORMATION FOR SEQ ID NO:24:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( v i i ) IMMEDIATE SOURCE:
        ( B ) CLONE: BMP-3

( i x ) FEATURE:
        ( A ) NAME/KEY: Protein
        ( B ) LOCATION: 1..120

( x i ) SEQUENCE DESCRIPTION: SEQ ID NO:24:

| Glu | Gln | Thr | Leu | Lys | Lys | Ala | Arg | Arg | Lys | Gln | Trp | Ile | Glu | Pro | Arg |
|---|---|---|---|---|---|---|---|---|---|---|---|---|---|---|---|
| 1 | | | | 5 | | | | | 10 | | | | | 15 | |

| Asn | Cys | Ala | Arg | Arg | Tyr | Leu | Lys | Val | Asp | Phe | Ala | Asp | Ile | Gly | Trp |
|---|---|---|---|---|---|---|---|---|---|---|---|---|---|---|---|
| | | | 20 | | | | | 25 | | | | | 30 | | |

| Ser | Glu | Trp | Ile | Ile | Ser | Pro | Lys | Ser | Phe | Asp | Ala | Tyr | Tyr | Cys | Ser |
|---|---|---|---|---|---|---|---|---|---|---|---|---|---|---|---|
| | | 35 | | | | | 40 | | | | | 45 | | | |

| Gly | Ala | Cys | Gln | Phe | Pro | Met | Pro | Lys | Ser | Leu | Lys | Pro | Ser | Asn | His |
|---|---|---|---|---|---|---|---|---|---|---|---|---|---|---|---|
| | 50 | | | | | 55 | | | | | 60 | | | | |

| Ala | Thr | Ile | Gln | Ser | Ile | Val | Arg | Ala | Val | Gly | Val | Val | Pro | Gly | Ile |
|---|---|---|---|---|---|---|---|---|---|---|---|---|---|---|---|
| 65 | | | | | 70 | | | | | 75 | | | | | 80 |

| Pro | Glu | Pro | Cys | Cys | Val | Pro | Glu | Lys | Met | Ser | Ser | Leu | Ser | Ile | Leu |
|---|---|---|---|---|---|---|---|---|---|---|---|---|---|---|---|
| | | | | 85 | | | | | 90 | | | | | 95 | |

| Phe | Phe | Asp | Glu | Asn | Lys | Asn | Val | Val | Leu | Lys | Val | Tyr | Pro | Asn | Met |
|---|---|---|---|---|---|---|---|---|---|---|---|---|---|---|---|
| | | | 100 | | | | | 105 | | | | | 110 | | |

| Thr | Val | Glu | Ser | Cys | Ala | Cys | Arg |
|---|---|---|---|---|---|---|---|
| | | | 115 | | | | 120 |

( 2 ) INFORMATION FOR SEQ ID NO:25:

( i ) SEQUENCE CHARACTERISTICS:
        ( A ) LENGTH: 116 amino acids
        ( B ) TYPE: amino acid
        ( D ) TOPOLOGY: linear ( i i ) MOLECULE TYPE: protein ( v i i ) IMMEDIATE SOURCE:
        ( B ) CLONE: MIS -continued ( i x ) FEATURE:
      ( A ) NAME/KEY: Protein
      ( B ) LOCATION: 1..116

( x i ) SEQUENCE DESCRIPTION: SEQ ID NO:25:

| Gly | Pro | Gly | Arg | Ala | Gln | Arg | Ser | Ala | Gly | Ala | Thr | Ala | Ala | Asp | Gly |
|---|---|---|---|---|---|---|---|---|---|---|---|---|---|---|---|
| 1 | | | | 5 | | | | | 10 | | | | | 15 | |
| Pro | Cys | Ala | Leu | Arg | Glu | Leu | Ser | Val | Asp | Leu | Arg | Ala | Glu | Arg | Ser |
| | | | 20 | | | | | 25 | | | | | 30 | | |
| Val | Leu | Ile | Pro | Glu | Thr | Tyr | Gln | Ala | Asn | Asn | Cys | Gln | Gly | Val | Cys |
| | | 35 | | | | | 40 | | | | | 45 | | | |
| Gly | Trp | Pro | Gln | Ser | Asp | Arg | Asn | Pro | Arg | Tyr | Gly | Asn | His | Val | Val |
| | 50 | | | | | 55 | | | | | 60 | | | | |
| Leu | Leu | Leu | Lys | Met | Gln | Ala | Arg | Gly | Ala | Ala | Leu | Ala | Arg | Pro | Pro |
| 65 | | | | | 70 | | | | | 75 | | | | | 80 |
| Cys | Cys | Val | Pro | Thr | Ala | Tyr | Ala | Gly | Lys | Leu | Leu | Ile | Ser | Leu | Ser |
| | | | | 85 | | | | | 90 | | | | | 95 | |
| Glu | Glu | Arg | Ile | Ser | Ala | His | His | Val | Pro | Asn | Met | Val | Ala | Thr | Glu |
| | | | 100 | | | | | 105 | | | | | 110 | | |
| Cys | Gly | Cys | Arg |
| | | | 115 |

( 2 ) INFORMATION FOR SEQ ID NO:26:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( v i i ) IMMEDIATE SOURCE:
        ( B ) CLONE: Inhibin-alpha ( i x ) FEATURE:
        ( A ) NAME/KEY: Protein
        ( B ) LOCATION: 1..122

( x i ) SEQUENCE DESCRIPTION: SEQ ID NO:26:

| Ala | Leu | Arg | Leu | Leu | Gln | Arg | Pro | Pro | Glu | Glu | Pro | Ala | Ala | His | Ala |
|---|---|---|---|---|---|---|---|---|---|---|---|---|---|---|---|
| 1 | | | | 5 | | | | | 10 | | | | | 15 | |
| Asn | Cys | His | Arg | Val | Ala | Leu | Asn | Ile | Ser | Phe | Gln | Glu | Leu | Gly | Trp |
| | | | 20 | | | | | 25 | | | | | 30 | | |
| Glu | Arg | Trp | Ile | Val | Tyr | Pro | Pro | Ser | Phe | Ile | Phe | His | Tyr | Cys | His |
| | | | 35 | | | | | 40 | | | | | 45 | | |
| Gly | Gly | Cys | Gly | Leu | His | Ile | Pro | Pro | Asn | Leu | Ser | Leu | Pro | Val | Pro |
| | 50 | | | | | 55 | | | | | 60 | | | | |
| Gly | Ala | Pro | Pro | Thr | Pro | Ala | Gln | Pro | Tyr | Ser | Leu | Leu | Pro | Gly | Ala |
| 65 | | | | | 70 | | | | | 75 | | | | | 80 |
| Gln | Pro | Cys | Cys | Ala | Ala | Leu | Pro | Gly | Thr | Met | Arg | Pro | Leu | His | Val |
| | | | | 85 | | | | | 90 | | | | | 95 | |
| Arg | Thr | Thr | Ser | Asp | Gly | Gly | Tyr | Ser | Phe | Lys | Tyr | Glu | Thr | Val | Pro |
| | | | 100 | | | | | 105 | | | | | 110 | | |
| Asn | Leu | Leu | Thr | Gln | His | Cys | Ala | Cys | Ile |
| | | 115 | | | | | 120 | | |

( 2 ) INFORMATION FOR SEQ ID NO:27:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( v i i ) IMMEDIATE SOURCE:
            ( B ) CLONE: Inhibin-beta-alpha ( i x ) FEATURE:
            ( A ) NAME/KEY: Protein
            ( B ) LOCATION: 1..122

( x i ) SEQUENCE DESCRIPTION: SEQ ID NO:27:

| His | Arg | Arg | Arg | Arg | Arg | Gly | Leu | Glu | Cys | Asp | Gly | Lys | Val | Asn | Ile |
|---|---|---|---|---|---|---|---|---|---|---|---|---|---|---|---|
| 1 | | | | 5 | | | | | 10 | | | | | 15 | |

| Cys | Cys | Lys | Lys | Gln | Phe | Phe | Val | Ser | Phe | Lys | Asp | Ile | Gly | Trp | Asn |
|---|---|---|---|---|---|---|---|---|---|---|---|---|---|---|---|
| | | | 20 | | | | 25 | | | | | 30 | | | |

| Asp | Trp | Ile | Ile | Ala | Pro | Ser | Gly | Tyr | His | Ala | Asn | Tyr | Cys | Glu | Gly |
|---|---|---|---|---|---|---|---|---|---|---|---|---|---|---|---|
| | | 35 | | | | | 40 | | | | | 45 | | | |

| Glu | Cys | Pro | Ser | His | Ile | Ala | Gly | Thr | Ser | Gly | Ser | Ser | Leu | Ser | Phe |
|---|---|---|---|---|---|---|---|---|---|---|---|---|---|---|---|
| | 50 | | | | 55 | | | | | | 60 | | | | |

| His | Ser | Thr | Val | Ile | Asn | His | Tyr | Arg | Met | Arg | Gly | His | Ser | Pro | Phe |
|---|---|---|---|---|---|---|---|---|---|---|---|---|---|---|---|
| 65 | | | | | 70 | | | | | 75 | | | | | 80 |

| Ala | Asn | Leu | Lys | Ser | Cys | Cys | Val | Pro | Thr | Lys | Leu | Arg | Pro | Met | Ser |
|---|---|---|---|---|---|---|---|---|---|---|---|---|---|---|---|
| | | | | 85 | | | | | 90 | | | | | 95 | |

| Met | Leu | Tyr | Tyr | Asp | Asp | Gly | Gln | Asn | Ile | Ile | Lys | Lys | Asp | Ile | Gln |
|---|---|---|---|---|---|---|---|---|---|---|---|---|---|---|---|
| | | | 100 | | | | | 105 | | | | | 110 | | |

| Asn | Met | Ile | Val | Glu | Glu | Cys | Gly | Cys | Ser |
|---|---|---|---|---|---|---|---|---|---|
| | | 115 | | | | | 120 | | |

( 2 ) INFORMATION FOR SEQ ID NO:28:

( i ) SEQUENCE CHARACTERISTICS:
            ( A ) LENGTH: 121 amino acids
            ( B ) TYPE: amino acid
            ( D ) TOPOLOGY: linear ( i i ) MOLECULE TYPE: protein ( v i i ) IMMEDIATE SOURCE:
            ( B ) CLONE: Inhibin-beta-beta ( i x ) FEATURE:
            ( A ) NAME/KEY: Protein
            ( B ) LOCATION: 1..121

( x i ) SEQUENCE DESCRIPTION: SEQ ID NO:28:

| His | Arg | Ile | Arg | Lys | Arg | Gly | Leu | Glu | Cys | Asp | Gly | Arg | Thr | Asn | Leu |
|---|---|---|---|---|---|---|---|---|---|---|---|---|---|---|---|
| 1 | | | | 5 | | | | | 10 | | | | | 15 | |

| Cys | Cys | Arg | Gln | Gln | Phe | Phe | Ile | Asp | Phe | Arg | Leu | Ile | Gly | Trp | Asn |
|---|---|---|---|---|---|---|---|---|---|---|---|---|---|---|---|
| | | | 20 | | | | | 25 | | | | | 30 | | |

| Asp | Trp | Ile | Ile | Ala | Pro | Thr | Gly | Tyr | Tyr | Gly | Asn | Tyr | Cys | Glu | Gly |
|---|---|---|---|---|---|---|---|---|---|---|---|---|---|---|---|
| | | 35 | | | | | 40 | | | | | 45 | | | |

| Ser | Cys | Pro | Ala | Tyr | Leu | Ala | Gly | Val | Pro | Gly | Ser | Ala | Ser | Ser | Phe |
|---|---|---|---|---|---|---|---|---|---|---|---|---|---|---|---|
| | 50 | | | | | 55 | | | | | 60 | | | | |

| His | Thr | Ala | Val | Val | Asn | Gln | Tyr | Arg | Met | Arg | Gly | Leu | Asn | Pro | Gly |
|---|---|---|---|---|---|---|---|---|---|---|---|---|---|---|---|
| 65 | | | | | 70 | | | | | 75 | | | | | 80 |

| Thr | Val | Asn | Ser | Cys | Cys | Ile | Pro | Thr | Lys | Leu | Ser | Thr | Met | Ser | Met |
|---|---|---|---|---|---|---|---|---|---|---|---|---|---|---|---|
| | | | | 85 | | | | | 90 | | | | | 95 | |

| Leu | Tyr | Phe | Asp | Asp | Glu | Tyr | Asn | Ile | Val | Lys | Arg | Asp | Val | Pro | Asn |
|---|---|---|---|---|---|---|---|---|---|---|---|---|---|---|---|
| | | | 100 | | | | | 105 | | | | | 110 | | |

| Met | Ile | Val | Glu | Glu | Cys | Gly | Cys | Ala |
|---|---|---|---|---|---|---|---|---|
| | | 115 | | | | | 120 | |

( 2 ) INFORMATION FOR SEQ ID NO:29:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( v i i ) IMMEDIATE SOURCE:
        ( B ) CLONE: TGF-beta-1

( i x ) FEATURE:
        ( A ) NAME/KEY: Protein
        ( B ) LOCATION: 1..115

( x i ) SEQUENCE DESCRIPTION: SEQ ID NO:29:

```
His  Arg  Arg  Ala  Leu  Asp  Thr  Asn  Tyr  Cys  Phe  Ser  Ser  Thr  Glu  Lys
  1                  5                       10                      15

Asn  Cys  Cys  Val  Arg  Gln  Leu  Tyr  Ile  Asp  Phe  Arg  Lys  Asp  Leu  Gly
                 20                      25                      30

Trp  Lys  Trp  Ile  His  Glu  Pro  Lys  Gly  Tyr  His  Ala  Asn  Phe  Cys  Leu
            35                      40                      45

Gly  Pro  Cys  Pro  Tyr  Ile  Trp  Ser  Leu  Asp  Thr  Gln  Tyr  Ser  Lys  Val
       50                      55                      60

Leu  Ala  Leu  Tyr  Asn  Gln  His  Asn  Pro  Gly  Ala  Ser  Ala  Ala  Pro  Cys
 65                      70                      75                      80

Cys  Val  Pro  Gln  Ala  Leu  Glu  Pro  Leu  Pro  Ile  Val  Tyr  Tyr  Val  Gly
                 85                      90                      95

Arg  Lys  Pro  Lys  Val  Glu  Gln  Leu  Ser  Asn  Met  Ile  Val  Arg  Ser  Cys
                100                     105                    110

Lys  Cys  Ser
           115
```

( 2 ) INFORMATION FOR SEQ ID NO:30:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( v i i ) IMMEDIATE SOURCE:
        ( B ) CLONE: TGF-beta-2

( i x ) FEATURE:
        ( A ) NAME/KEY: Protein
        ( B ) LOCATION: 1..115

( x i ) SEQUENCE DESCRIPTION: SEQ ID NO:30:

```
Lys  Lys  Arg  Ala  Leu  Asp  Ala  Ala  Tyr  Cys  Phe  Arg  Asn  Val  Gln  Asp
  1                  5                       10                      15

Asn  Cys  Cys  Leu  Arg  Pro  Leu  Tyr  Ile  Asp  Phe  Lys  Arg  Asp  Leu  Gly
                 20                      25                      30

Trp  Lys  Trp  Ile  His  Glu  Pro  Lys  Gly  Tyr  Asn  Ala  Asn  Phe  Cys  Ala
            35                      40                      45

Gly  Ala  Cys  Pro  Tyr  Leu  Trp  Ser  Ser  Asp  Thr  Gln  His  Ser  Arg  Val
       50                      55                      60

Leu  Ser  Leu  Tyr  Asn  Thr  Ile  Asn  Pro  Glu  Ala  Ser  Ala  Ser  Pro  Cys
 65                      70                      75                      80

Cys  Val  Ser  Gln  Asp  Leu  Glu  Pro  Leu  Thr  Ile  Leu  Tyr  Tyr  Ile  Gly
                 85                      90                      95

Lys  Thr  Pro  Lys  Ile  Glu  Gln  Leu  Ser  Asn  Met  Ile  Val  Lys  Ser  Cys
```

-continued

```
                        100                      105                     110
Lys  Cys  Ser
          115
```

( 2 ) INFORMATION FOR SEQ ID NO:31:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( v i i ) IMMEDIATE SOURCE:
        ( B ) CLONE: TGF-beta-3

( i x ) FEATURE:
        ( A ) NAME/KEY: Protein
        ( B ) LOCATION: 1..115

( x i ) SEQUENCE DESCRIPTION: SEQ ID NO:31:

```
Lys  Lys  Arg  Ala  Leu  Asp  Thr  Asn  Tyr  Cys  Phe  Arg  Asn  Leu  Glu  Glu
 1              5                        10                       15
Asn  Cys  Cys  Val  Arg  Pro  Leu  Tyr  Ile  Asp  Phe  Arg  Gln  Asp  Leu  Gly
               20                       25                       30
Trp  Lys  Trp  Val  His  Glu  Pro  Lys  Gly  Tyr  Tyr  Ala  Asn  Phe  Cys  Ser
          35                       40                       45
Gly  Pro  Cys  Pro  Tyr  Leu  Arg  Ser  Ala  Asp  Thr  Thr  His  Ser  Thr  Val
     50                       55                       60
Leu  Gly  Leu  Tyr  Asn  Thr  Leu  Asn  Pro  Glu  Ala  Ser  Ala  Ser  Pro  Cys
65                       70                       75                       80
Cys  Val  Pro  Gln  Asp  Leu  Glu  Pro  Leu  Thr  Ile  Leu  Tyr  Tyr  Val  Gly
                    85                       90                       95
Arg  Thr  Pro  Lys  Val  Glu  Gln  Leu  Ser  Asn  Met  Val  Val  Lys  Ser  Cys
               100                      105                      110
Leu  Cys  Ser
          115
```

( 2 ) INFORMATION FOR SEQ ID NO:32:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..118
        ( D ) OTHER INFORMATION: /note= "Xaa at positions 2 and 3 is
              any amino acid"

( x i ) SEQUENCE DESCRIPTION: SEQ ID NO:32:

```
Arg  Xaa  Xaa  Arg
 1
```

GROWTH DIFFERENTIATION FACTOR-8 (GDF-8) AND POLYNUCLEOTIDES ENCODING SAME

This application is a 371 application of PCT US94/03019, filed Mar. 18, 1994, and a continuation-in-part application of the U.S. application Ser. No. 08/033,923 filed on Mar. 19, 1993. now abandoned.

BACKGROUND OF THE INVENTION

1. Field of the Invention

The invention relates generally to growth factors and specifically to a new member of the transforming growth factor beta (TGF-β) superfamily, which is denoted, growth differentiation factor-8 (GDF-8).

2. Description of Related Art

The transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., Nature, 345:167, 1990), Drosophila decapentaplegic (DPP) gene product, which is required for dorsal-ventral axis formation and morphogenesis of the imaginal disks (Padgett, et al., Nature, 325:81–84, 1987), the Xenopus Vg-1 gene product, which localizes to the vegetal pole of eggs ((Weeks, et al., Cell, 51:861–867, 1987), the activins (Mason, et al., Biochem, Biophys. Res. Commun., 135:957–964, 1986), which can induce the formation of mesoderm and anterior structures in Xenopus embryos (Thomsen, et al., Cell, 63:485, 1990), and the bone morphogenetic proteins (BMPs, osteogenin, OP-1) which can induce de novo cartilage and bone formation (Sampath, et al., J. Biol. Chem., 265:13198, 1990). The TGF-βs can influence a variety of differentiation processes, including adipogenesis, myogenesis, chondrogenesis, hematopoiesis, and epithelial cell differentiation (for review, see Massague, Cell 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray, A., and Maston, A., Science, 247:1328, 1990). Additional studies by Hammonds, et al., (Molec. Endocrin. 5:149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling, et al., Nature, 321:779, 1986) and the TGF-βs (Cheifetz, et al., Cell, 48:409, 1987), heterodimers have also been detected, and these appear to have different biological properties than the respective homodimers.

Identification of new factors that are tissue-specific in their expression pattern will provide a greater understanding of that tissue's development and function.

SUMMARY OF THE INVENTION

-The present invention provides a cell growth and differentiation factor, GDF-8, a polynucleotide sequence which encodes the factor, and antibodies which are immunoreactive with the factor. This factor appears to relate to various cell proliferative disorders, especially those involving those involving muscle, nerve, and adipose tissue.

Thus, in one embodiment, the invention provides a method for detecting a cell proliferative disorder of muscle, nerve, or fat origin and which is associated with GDF-8. In another embodiment, the invention provides a method for treating a cell proliferative disorder by suppressing or enhancing GDF-8 activity.

BRIEF DESCRIPTION OF THE DRAWINGS

FIGS. 2(a–b) shows nucleotide and predicted amino acid sequences of murine GDF-8 (FIG. 2a; SEQ ID NOS:5 and 6, respectively) and human GDF-8 (FIG. 2b; SEQ ID NOS:7 and 8, respectively). The putative dibasic processing sites in the murine sequence are boxed.

FIG. 3 shows the alignment of the C-terminal sequences of GDF-8 with other members of the TGF-β superfamily (SEQ ID NOS:14 and 18–31). The conserved cysteine residues are boxed. Dashes denote gaps introduced in order to maximize alignment.

FIG. 4 shows amino acid homologies among different members of the TGF-β superfamily. Numbers represent percent amino acid identities between each pair calculated from the first conserved cysteine to the C-terminus. Boxes represent homologies among highly-related members within particular subgroups.

FIGS. 5(a–d) shows the sequence of GDF-8. Nucleotide and amino acid sequences of murine (FIG. 5a and FIG. 5b) and human (FIGS. 5c and 5d) GDF-8 cDNA clones are shown. Numbers indicate nucleotide position relative to the 5' end. Consensus N-linked glycosylation signals are shaded. The putative RXXR (SEQ ID NO:32) proteolytic cleavage sites are boxed.

FIG. 7 shows a comparison of murine and human GDF-8 amino acid sequences (SEQ ID NOS:12 and 14, respectively). The predicted murine sequence is shown in the top lines and the predicted human sequence is shown in the bottom lines. Numbers indicate amino acid position relative to the N-terminus. Identities between the two sequences are denoted by a vertical line.

DETAILED DESCRIPTION OF THE INVENTION

Figure 1:
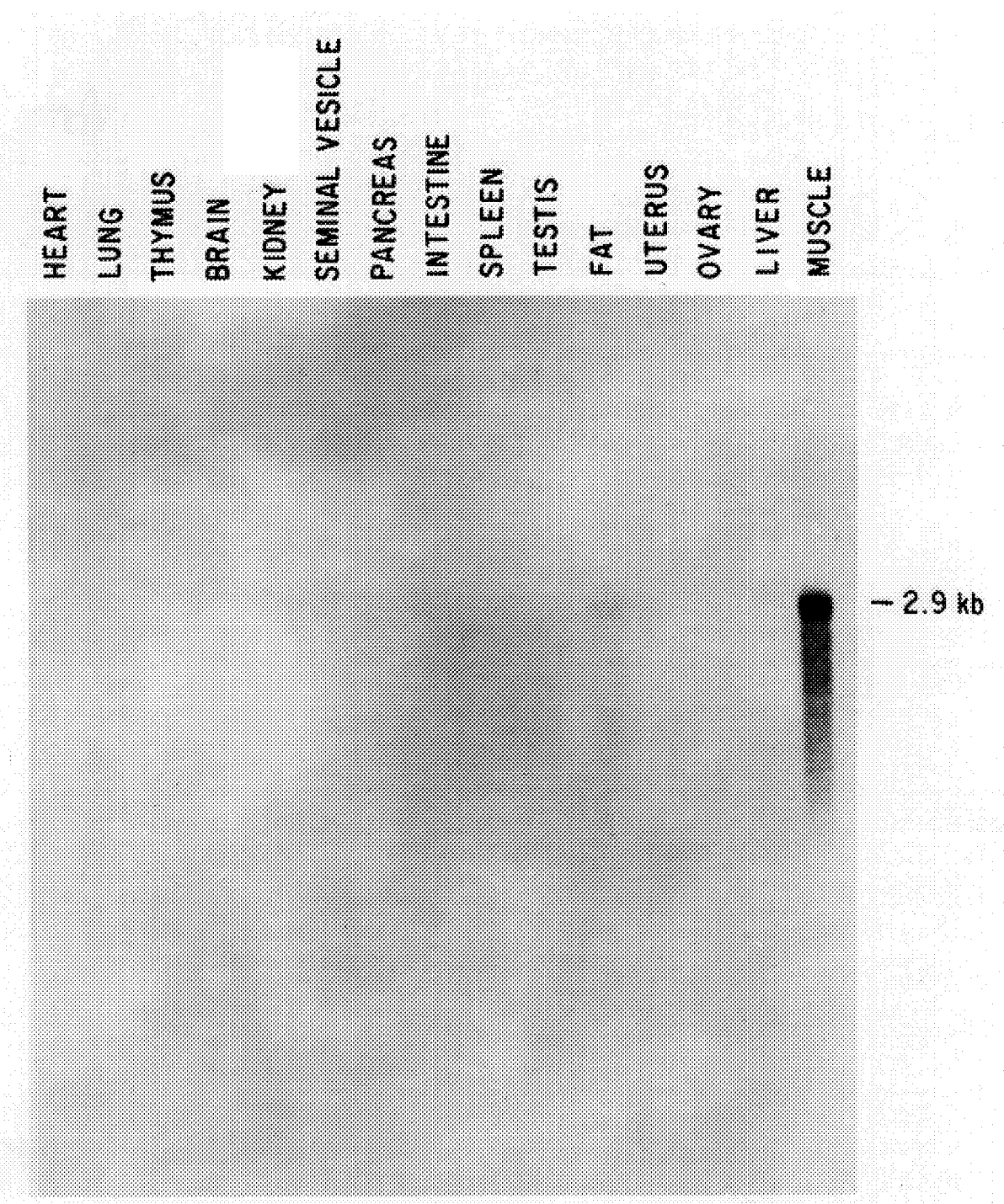
FIG. 1 is a Northern blot showing expression of GDF-8 mRNA in adult tissues. The probe was a partial murine GDF-8 clone.

The present invention provides a growth and differentiation factor, GDF-8 and a polynucleotide sequence encoding GDF-8. GDF-8 is expressed at highest levels in muscle and at lower levels in adipose tissue. In one embodiment, the invention provides a method for detection of a cell proliferative disorder of muscle, nerve, or fat origin which is associated with GDF-8 expression. In another embodiment, the invention provides a method for treating a cell proliferative disorder by using an agent which suppresses or enhances GDF-8 activity.

The TGF-β superfamily consists of multifunctional polypeptides that control proliferation, differentiation, and other functions in many cell types. Many of the peptides have regulatory, both positive and negative, effects on other peptide growth factors. The structural homology between the GDF-8 protein of this invention and the members of the TGF-β family, indicates that GDF-8 is a new member of the family of growth and differentiation factors. Based on the known activities of many of the other members, it can be expected that GDF-8 will also possess biological activities that will make it useful as a diagnostic and therapeutic reagent.

In particular, certain members of this superfamily have expression patterns or possess activities that relate to the function of the nervous system. For example, the inhibins and activins have been shown to be expressed in the brain (Meunier, et al., Proc. Natl. Acad. Sci., U.S.A., 85:247, 1988; Sawchenko, et al., Nature, 334:615, 1988), and activin has been shown to be capable of functioning as a nerve cell survival molecule (Schubert, et al., Nature, 344:868, 1990). Another family member, namely, GDF-1, is nervous system-specific in its expression pattern (Lee, S. J., Proc. Natl. Acad. Sci., U.S.A., 88:4250, 1991), and certain other family members, such as Vgr-1 (Lyons, et al., Proc. Natl Acad. Sci., U.S.A., 86:4554, 1989; Jones, et al., Development, 111:531, 1991), OP-1 (Ozkaynak, et al., J. Biol. Chem., 267:25220, 1992), and BMP-4 (Jones, et al., Development, 111:531, 1991), are also known to be expressed in the nervous system. Because it is known that skeletal muscle produces a factor or factors that promote the survival of motor neurons (Brown, Trends Neurosci., 7:10, 1984), the expression of GDF-8 in muscle suggests that one activity of GDF-8 may be as a trophic factor for neurons. In this regard, GDF-8 may have applications in the treatment of neurodegenerative diseases, such as amyotrophic lateral sclerosis, or in maintaining cells or tissues in culture prior to transplantation.

GDF-8 may also have applications in treating disease processes involving muscle, such as in musculodegenerative diseases or in tissue repair due to trauma. In this regard, many other members of the TGF-β family are also important mediators of tissue repair. TGF-β has been shown to have marked effects on the formation of collagen and to cause a striking angiogenic response in the newborn mouse (Roberts, et al., Proc. Natl. Acad. Sci., U.S.A. 83:4167, 1986). TGF-β has also been shown to inhibit the differentiation of myoblasts in culture (Massague, et al., Proc. Natl. Acad. Sci., U.S.A. 83:8206, 1986). Moreover, because myoblast cells may be used as a vehicle for delivering genes to muscle for gene therapy, the properties of GDF-8 could be exploited for maintaining cells prior to transplantation or for enhancing the efficiency of the fusion process.

The expression of GDF-8 in adipose tissue also raises the possibility of applications for GDF-8 in the treatment of obesity or of disorders related to abnormal proliferation of adipocytes. In this regard, TGF-β has been shown to be a potent inhibitor of adipocyte differentiation in vitro (Ignotz and Massague, Proc. Natl. Acad. Sci., U.S.A. 82:8530, 1985).

The term "substantially pure" as used herein refers to GDF-8 which is substantially free of other proteins, lipids, carbohydrates or other materials with which it is naturally associated. One skilled in the art can purify GDF-8 using standard techniques for protein purification. The substantially pure polypeptide will yield a single major band on a non-reducing polyacrylamide gel. The purity of the GDF-8 polypeptide can also be determined by amino-terminal amino acid sequence analysis. GDF-8 polypeptide includes functional fragments of the polypeptide, as long as the activity of GDF-8 remains. Smaller peptides containing the biological activity of GDF-8 are included in the invention.

The invention provides polynucleotides encoding the GDF-8 protein. These polynucleotides include DNA, cDNA and RNA sequences which encode GDF-8. It is understood that all polynucleotides encoding all or a portion of GDF-8 are also included herein, as long as they encode a polypeptide with GDF-8 activity. Such polynucleotides include naturally occurring, synthetic, and intentionally manipulated polynucleotides. For example, GDF-8 polynucleotide may be subjected to site-directed mutagenesis. The polynucleotide sequence for GDF-8 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-8 polypeptide encoded by the nucleotide sequence is functionally unchanged.

Specifically disclosed herein is a genomic DNA sequence containing a portion of the GDF-8 gene. The sequence contains an open reading frame corresponding to the predicted C-terminal region of the GDF-8 precursor protein. The encoded polypeptide is predicted to contain two potential proteolytic processing sites (KR and RR). Cleavage of the precursor at the downstream site would generate a mature biologically active C-terminal fragment of 109 amino acids with a predicted molecular weight of approximately 12,400. Also, disclosed are full length murine and human GDF-8 cDNA sequences. The murine pre-pro-GDF-8 protein is 376 amino acids in length, which is encoded by a 2676 base pair nucleotide sequence, beginning at nucleotide 104 and extending to a TGA stop codon at nucleotide 1232. The human GDF-8 protein is 375 amino acids and is encoded by a 2743 base pair sequence, with the open reading frame beginning at nucleotide 59 and extending to nucleotide 1184.

The C-terminal region of GDF-8 following the putative proteolytic processing site shows significant homology to the known members of the TGF-β superfamily. The GDF-8 sequence contains most of the residues that are highly conserved in other family members (see FIG. 3). Like the TGF-βs and inhibin βs, GDF-8 contains an extra pair of cysteine residues in addition to the 7 cysteines found in virtually all other family members. Among the known family members, GDF-8 is most homologous to Vgr-1 (45% sequence identity) (see FIG. 4).

Minor modifications of the recombinant GDF-8 primary amino acid sequence may result in proteins which have substantially equivalent activity as compared to the GDF-8 polypeptide described herein. Such modifications may be deliberate, as by site-directed mutagenesis, or may be spontaneous. All of the polypeptides produced by these modifications are included herein as long as the biological activity of GDF-8 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-8 biological activity.

The nucleotide sequence encoding the GDF-8 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the GDF-8 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

The development of specific DNA sequences encoding GDF-8 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., Nucl. Acid Res., 11:2325, 1983).

A cDNA expression library, such as lambda gt11, can be screened indirectly for GDF-8 peptides having at least one epitope, using antibodies specific for GDF-8. Such antibodies can be either polyclonally or monoclonally derived and used to detect expression product indicative of the presence of GDF-8 cDNA.

DNA sequences encoding GDF-8 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

Methods of stable transfer, meaning that the foreign DNA is continuously maintained in the host, are known in the art.

In the present invention, the GDF-8 polynucleotide sequences may be inserted into a recombinant expression vector. The term "recombinant expression vector" refers to a plasmid, virus or other vehicle known in the art that has been manipulated by insertion or incorporation of the GDF-8 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding GDF-8 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Preferably, the mature C-terminal region of GDF-8 is expressed from a cDNA clone containing the entire coding sequence of GDF-8. Alternatively, the C-terminal portion of GDF-8 can be expressed as a fusion protein with the pro-region of another member of the TGF-β family or co-expressed with another pro-region (see for example, Hammonds, et al., Molec. Endocrin. 5:149, 1991; Gray, A., and Mason, A., Science, 247:1328, 1990).

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-8 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, Eukaryotic Viral Vectors, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-8 polypeptide or functional fragments thereof. Antibody which consists essentially of pooled monoclonal antibodies with differer epitopic specificities, as well as distinct monoclonal antibody preparations are provided. Monoclonal antibodies are made from antigen containing fragments of the -protein by methods well known to those skilled in the art (Kohler, et al., Nature, 256:495, 1975). The term antibody as used in this invention is meant to include intact molecules as well as fragments thereof, such as Fab and $F(ab')_2$, which are capable of binding an epitopic determinant on GDF-8.

The term "cell-proliferative disorder" denotes malignant as well as non-malignant cell populations which often appear to differ from the surrounding tissue both morphologically and genotypically. Malignant cells (i.e. cancer) develop as a result of a multistep process. The GDF-8 polynucleotide that is an antisense molecule is useful in treating malignancies of the various organ systems, particularly, for example, cells in muscle or adipose tissue. Essentially, any disorder which is etiologically linked to altered expression of GDF-8 could be considered susceptible to treatment with a GDF-8 suppressing reagent. One such disorder is a malignant cell proliferative disorder, for example.

The invention provides a method for detecting a cell proliferative disorder of muscle or adipose tissue which comprises contacting an anti-GDF-8 antibody with a cell suspected of having a GDF-8 associated disorder and detecting binding to the antibody. The antibody reactive with GDF-8 is labeled with a compound which allows detection of binding to GDF-8. For purposes of the invention, an antibody specific for GDF-8 polypeptide may be used to detect the level of GDF-8 in biological fluids and tissues. Any specimen containing a detectable amount of antigen can be used. A preferred sample of this invention is muscle tissue. The level of GDF-8 in the suspect cell can be compared with the level in a normal cell to determine whether the subject has a GDF-8-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-8-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-8-associated disease is effective. The term "ameliorate" denotes a lessening of the detrimental effect of the GDF-8-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Thus, where a cell-proliferative disorder is associated with the expression of GDF-8, nucleic acid sequences that interfere with GDF-8 expression at the translational level can be used. This approach utilizes, for example, antisense nucleic acid and ribozymes to block translation of a specific GDF-8 mRNA, either by masking that mRNA with an antisense nucleic acid or by cleaving it with a ribozyme. Such disorders include neurodegenerative diseases, for example.

Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target GDF-8-producing cell. The use of antisense methods to inhibit the in vitro translation of genes is well known in the art (Marcus-Sakura, Anal. Biochem., 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders which are mediated by GDF-8 protein. Such therapy would achieve its therapeutic effect by introduction of the GDF-8 antisense polynucleotide into cells having the proliferative disorder. Delivery of antisense GDF-8 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-8 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the GDF-8 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to $\Psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-8 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-8 in muscle and adipose tissue, there are a variety of applications using the polypeptide, polynucleotide, and antibodies of the invention, related to these tissues. Such applications include treatment of cell proliferative disorders involving these and other tissues, such as neural tissue. In addition, GDF-8 may be useful in various gene therapy procedures.

The data in Example 6 shows that the human GDF-8 gene is located on chromosome 2. By comparing the chromosomal location of GDF-8 with the map positions of various human disorders, it should be possible to determine whether mutations in the GDF-8 gene are involved in the etiology of human diseases. For example, an autosomal recessive form of juvenile amyotrophic lateral sclerosis has been shown to map to chromosome 2 (Hentati, et al., Neurology, 42 [Suppl.3]:201, 1992). More precise mapping of GDF-8 and analysis of DNA from these patients may indicate that GDF-8 is, in fact, the gene affected in this disease. In addition, GDF-8 is useful for distinguishing chromosome 2 from other chromosomes.

The following examples are intended to illustrate but not limit the invention. While they are typical of those that might be used, other procedures known to those skilled in the art may alternatively be used.

EXAMPLE 1

IDENTIFICATION AND ISOLATION OF A NOVEL TGF-β FAMILY MEMBER

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on mouse genomic DNA followed by subcloning the PCR products using restriction sites placed at the 5' ends of the primers, picking individual E. coli colonies carrying these subcloned inserts, and using a combination of random sequencing and hybridization analysis to eliminate known members of the superfamily.

GDF-8 was identified from a mixture of PCR products obtained with the primers

SJL141:
5'-CCGGAATTCGGITGG(G/C/A)A(G/A/T/C)A(T/C)TGG(A/G)TI(A/G)TI(T/G)CICC-3' (SEQ ID NO: 1)

SJL147:
5'-CCGGAATTC(G/A)CAI(G/C)C(G/A)CA(G/A)CT(G/A/T/C)TCIACI(G/A)(T/C)CAT-3' (SEQ ID NO:2)

PCR products of approximately 2 µg mouse genomic DNA at 94° C. for 1 min, 50° C. for 2 min, and 72° C. for 2 min for 40 cycles.

PCR products of approximately 280 bp were gel-purified, digested with Eco RI, gel-purified again, and subcloned in the Bluescript vector (Stratagene, San Diego, Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from non-hybridzing colonies for sequence analysis.

The primer combination of SJL141 and SJL147, encoding the amino acid sequences GW(H/Q/N/K/D/E)(D/N)W(V/I/M)(V/I/M)(A/S)P (SEQ ID NO:9) and M(V/I/M/T/A)V(D/E)SC(G/A)C (SEQ ID NO:10), respectively, yielded four previously identified sequences (BMP-4, inhibin βB, GDF-3 and GDF-5) and one novel sequence, which was designated GDF-8, among 110 subclones analyzed.

Human GDF-8 was isolated using the primers:

ACM13: (SEQ ID NO: 3)
5'-CGCGGATCCAGAAGTCAAGGTGACAGACACAC-3' ;

and

ACM14: (SEQ ID NO: 4)
5'-CGCGGATCCTCCTCATGAGCACCCACAGCGGTC-3'

PCR using these primers was carried out with one µg human genomic DNA at 94° C. for 1 min, 58° C. for 2 min, and 72° C. for 2 min for 30 cycles. The PCR product was digested with Bam HI, gel-purified, and subcloned in the Bluescript vector (Stratagene, San Francisco, Calif.).

EXAMPLE 2

EXPRESSION PATTERN AND SEQUENCE OF GDF-8

To determine the expression pattern of GDF-8, RNA samples prepared from a variety of adult tissues were screened by Northern analysis. RNA isolation and Northern analysis were carried out as described previously (Lee, S.-J., Mol. Endocrinol., 4:1034, 1990) except that hybridization was carried out in 5× SSPE, 10% dextran sulfate, 50% formamide, 1% SDS, 200 µg/ml salmon DNA, and 0.1% each of bovine serum albumin, ficoll, and polyvinylpyrrolidone. Five micrograms of twice poly A-selected RNA prepared from each tissue (except for muscle, for which only 2 µg RNA was used) were electrophoresed on formaldehyde gels, blotted, and probed with GDF-8. As shown in FIG. 1, the GDF-8 probe detected a single mRNA species expressed at highest levels in muscle and at significantly lower levels in adipose tissue.

To obtain a larger segment of the GDF-8 gene, a mouse genomic library was screened with a probe derived from the GDF-8 PCR product. The partial sequence of a GDF-8 genomic clone is shown in FIG. 2a. The sequence contains an open reading frame corresponding to the predicted C-terminal region of the GDF-8 precursor protein. The predicted GDF-8 sequence contains two potential proteolytic processing sites, which are boxed. Cleavage of the precursor at the second of these sites would generate a mature C-terminal fragment 109 amino acids in length with a predicted molecular weight of 12,400. The partial sequence of human GDF-8 is shown in FIG. 2b. Assuming no PCR-induced errors during the isolation of the human clone, the human and mouse amino acid sequences in this region are 100% identical.

The C-terminal region of GDF-8 following the putative proteolytic processing site shows significant homology to the known members of the TGF-β superfamily (FIG. 3). FIG. 3 shows the alignment of the C-terminal sequences of GDF-8 with the corresponding regions of human GDF-1 (Lee, Proc. Natl. Acad. Sci. U.S.A., 88:4250–4254, 1991), human BMP-2 and 4 (Wozney, et al., Science, 242:1528–1534, 1988), human Vgr-1 (Celeste, et al., Proc. Natl. Acad. Sci. U.S.A., 87:9843–9847, 1990), human OP-1 (Ozkaynak, et al., EMBO J., 9:2085–2093, 1990), human BMP-5 (Celeste, et al., Proc. Natl. Acad. Sci. U.S.A., 87:9843–9847, 1990), human BMP-3 (Wozney, et al., Science, 242:1528–1534,1988), human MIS (Cate, et al., Cell, 45:685–698, 1986), human inhibin alpha, βA, and βB (Mason, et al., Biochem, Biophys. Res. Commun., 135:957–964, 1986), human TGF-:1 (Derynck, et al., Nature, 316:701–705, 1985), humanTGF-β2 (deMartin, et al., EMBO J., 6:3673–3677, 1987), and human TGF-β3 (ten Dijke, et al., Proc. Natl. Acad. Sci. U.S.A., 85:4715–4719, 1988). The conserved cysteine residues are boxed. Dashes denote gaps introduced in order to maximize the alignment.

GDF-8 contains most of the residues that are highly conserved in other family members, including the seven cysteine residues with their characteristic spacing. Like the TGF-βs and inhibin βs, GDF-8 also contains two additional cysteine residues. In the case of TGF-β2, these two additional cysteine residues are known to form an intramolecular disulfide bond (Daopin, et al., Science, 257:369, 1992; Schlunegger and Grutter, Nature, 358:430, 1992).

FIG. 4 shows the amino acid homologies among the different members of the TGF-β superfamily. Numbers represent percent amino acid identities between each pair calculated from the first conserved cysteine to the C-terminus. Boxes represent homologies among highly-related members within particular subgroups. In this region, GDF-8 is most homologous to Vgr-1 (45% sequence identity).

EXAMPLE 3

ISOLATION OF cDNA CLONES ENCODING MURINE AND HUMAN GDF-8

In order to isolate full-length cDNA clones encoding murine and human GDF-8, cDNA libraries were prepared in the lambda ZAP II vector (Stratagene) using RNA prepared from skeletal muscle. From 5 µg of twice poly A-selected RNA prepared from murine and human muscle, cDNA libraries consisting of 4.4 million and 1.9 million recombinant phage, respectively, were constructed according to the instructions provided by Stratagene. These libraries were screened without amplification. Library screening and characterization of cDNA inserts were carried out as described previously (Lee, Mol. Endocrinol, 4:1034–1040).

Figure 6A:
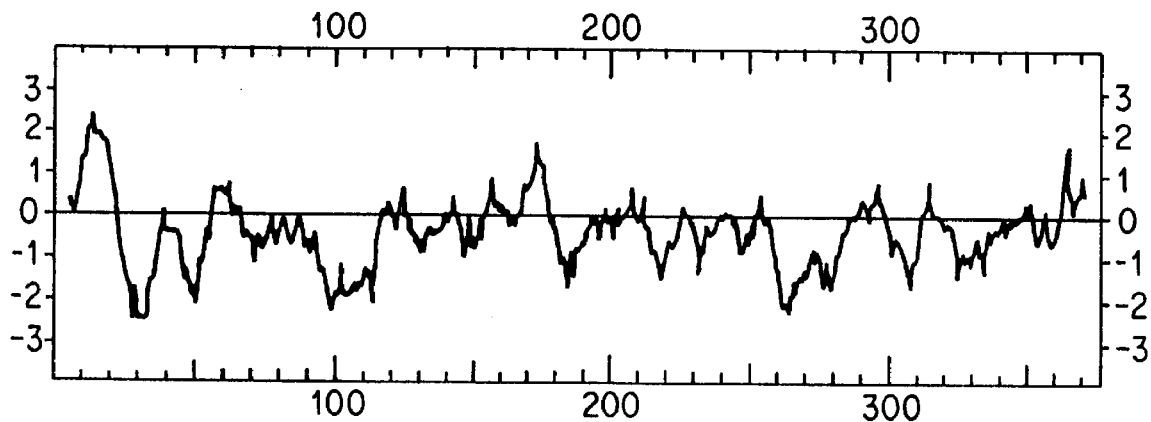
FIGS. 6(a–b) shows a hydropathicity profile of GDF-8. Average hydrophobicity values for murine (FIG. 6a) and human (FIG. 6b) GDF-8 were calculated using the method of Kyte and Doolittle (J. Mol. Biol., 157:105–132, 1982). Positive numbers indicate increasing hydrophobicity.

From $2.4 \times 10^6$ recombinant phage screened from the murine muscle cDNA library, greater than 280 positive phage were identified using a murine GDF-8 probe derived from a genomic clone, as described in Example 1. The entire nucleotide sequence of the longest cDNA insert analyzed is shown in FIG. 5a and SEQ ID NO:11. The 2676 base pair sequence contains a single long open reading frame beginning with a methionine codon at nucleotide 104 and extending to a TGA stop codon at nucleotide 1232. Upstream of the putative initiating methionine codon is an in-frame stop codon at nucleotide 23. The predicted pre-pro-GDF-8 protein is 376 amino acids in length. The sequence contains a core of hydrophobic amino acids at the N-terminus suggestive of a signal peptide for secretion (FIG. 6a), one potential N-glycosylation site at asparagine 72, a putative RXXR (SEQ ID NO:32) proteolytic cleavage site at amino acids 264–267, and a C-terminal region showing significant homology to the known members of the TGF-β superfamily. Cleavage of the precursor protein at the putative RXXR (SEQ ID NO:32) site would generate a mature C-terminal GDF-8 fragment 109 amino acids in length with a predicted molecular weight of approximately 12,400.

Figure 6B:
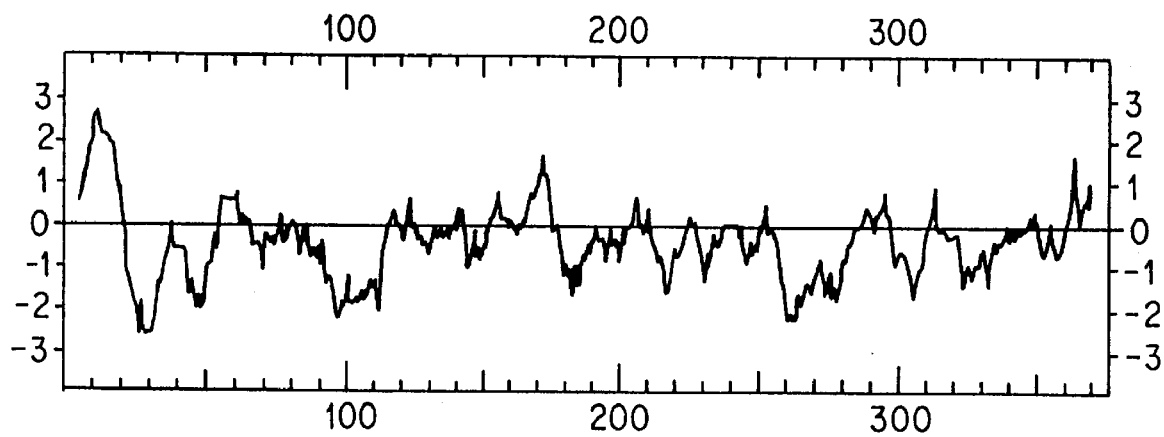

From $1.9 \times 10^6$ recombinant phage screened from the human muscle cDNA library, 4 positive phage were identified using a human GDF-8 probe derived by polymerase chain reaction on human genomic DNA. The entire nucleotide sequence of the longest cDNA insert is shown in FIG. 5b and SEQ ID NO:13. The 2743 base pair sequence contains a single long open reading frame beginning with a methionine codon at nucleotide 59 and extending to a TGA stop codon at nucleotide 1184. The predicted pre-pro-GDF-8 protein is 375 amino acids in length. The sequence contains a core of hydrophobic amino acids at the N-terminus suggestive of a signal peptide for secretion (FIG. 6b), one potential N-glycosylation site at asparagine 71, and a putative RXXR (SEQ ID NO:32) proteolytic cleavage site at amino acids 263–266. FIG. 7 shows a comparison of the predicted murine (top) and human (bottom) GDF-8 amino acid sequences. Numbers indicate amino acid position relative to the N-terminus. Identities between the two sequences are denoted by a vertical line. Murine and human GDF-8 are approximately 94% identical in the predicted pro-regions and 100% identical following the predicted RXXR (SEQ ID NO:32) cleavage sites.

EXAMPLE 4

PREPARATION OF ANTIBODIES AGAINST GDF-8 AND EXPRESSION OF GDF-8 IN MAMMALIAN CELLS

Figure 8:
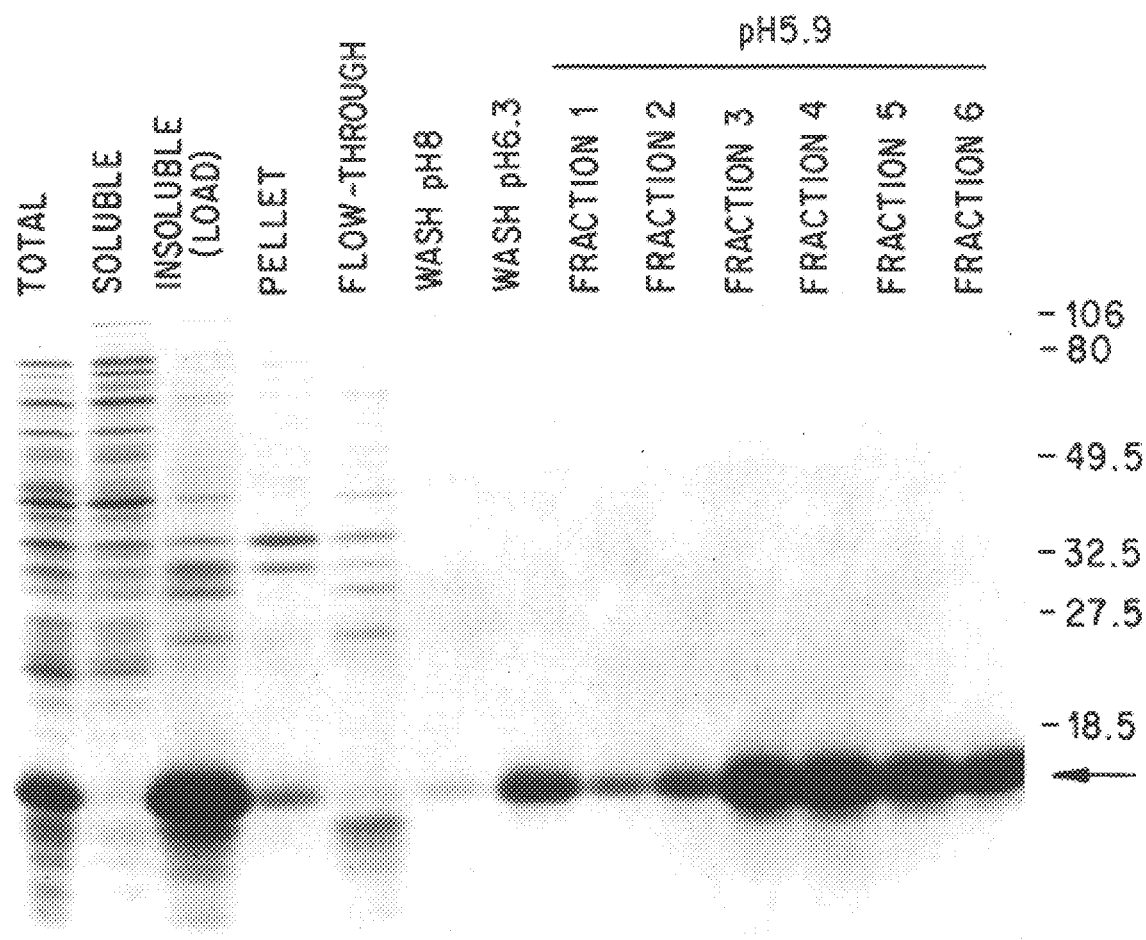
FIG. 8 shows the expression of GDF-8 in bacteria. BL21 (DE3) (pLysS) cells carrying a pRSET/GDF-8 expression plasmid were induced with isopropylthio-β-galactoside, and the GDF-8 fusion protein was purified by metal chelate chromatography. Lanes: total=total cell lysate; soluble= soluble protein fraction; insoluble=insoluble protein fraction (resuspended in 10 mM Tris pH 8.0, 50 mM sodium phosphate, 8M urea, and 10 mM β-mercaptoethanol [buffer B]) loaded onto the column; pellet=insoluble protein fraction discarded before loading the column; flowthrough= proteins not bound by the column; washes=washes carried out in buffer B at the indicated pH's. Positions of molecular weight standards are shown at the right. Arrow indicates the position of the GDF-8 fusion protein.

In order to prepare antibodies against GDF-8, GDF-8 antigen was expressed as a fusion protein in bacteria. A portion of murine GDF-8 cDNA spanning amino acids 268–376 (mature region) was inserted into the pRSET vector (Invitrogen) such that the GDF-8 coding sequence was placed in frame with the initiating methionine codon present in the vector; the resulting construct created an open reading frame encoding a fusion protein with a molecular weight of approximately 16,600. The fusion construct was transformed into BL21 (DE3) (pLysS) cells, and expression of the fusion protein was induced by treatment with isopropylthio-β-galactoside as described (Rosenberg, et al., Gene, 56:125–135). The fusion protein was then purified by metal chelate chromatography according to the instructions provided by Invitrogen. A Coomassie blue-stained gel of unpurified and purified fusion proteins is shown in FIG. 8.

The purified fusion protein was used to immunize both rabbits and chickens. Immunization of rabbits was carried out by Spring Valley Labs (Sykesville, Md.), and immunization of chickens was carried out by HRP, Inc. (Denver, Pa.). Western analysis of sera both from immunized rabbits and from immunized chickens demonstrated the presence of antibodies directed against the fusion protein.

To express GDF-8 in mammalian cells, the murine GDF-8 cDNA sequence from nucleotides 48-1303 was cloned in both orientations downstream of the metallothionein I promoter in the pMSXND expression vector; this vector contains processing signals derived from SV40, a dihydrofolate reductase gene, and a gene conferring resistance to the antibiotic G418 (Lee and Nathans, J. Biol. Chem., 263:3521–3527). The resulting constructs were transfected into Chinese hamster ovary cells, and stable tranfectants were selected in the presence of G418. Two milliliters of conditioned media prepared from the G418-resistant cells were dialyzed, lyophilized, electrophoresed under denaturing, reducing conditions, transferred to nitrocellulose, and incubated with anti-GDF-8 antibodies (described above) and [$^{125}$I]iodoproteinA.

Figure 9:
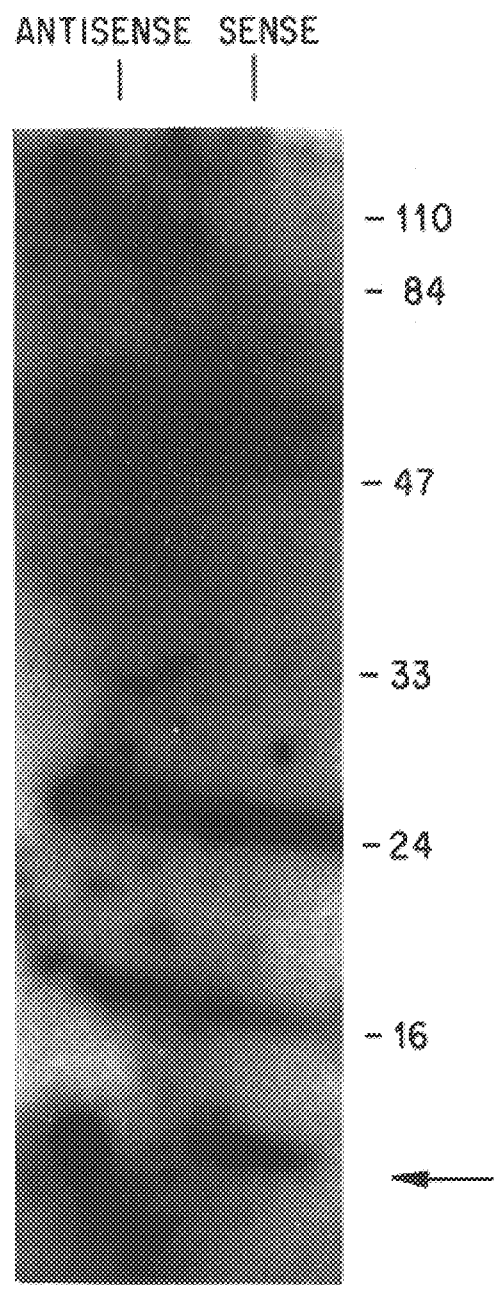
FIG. 9 shows the expression of GDF-8 in mammalian cells. Chinese hamster ovary cells were transfected with pMSXND/GDF-8 expression plasmids and selected in G418. Conditioned media from G418-resistant cells (prepared from cells transfected with constructs in which GDF-8 was cloned in either the antisense or sense orientation) were concentrated, electrophoresed under reducing conditions, blotted, and probed with anti-GDF-8 antibodies and [$^{125}$I]iodoproteinA. Arrow indicates the position of the processed GDF-8 protein.

As shown in FIG. 9, the rabbit GDF-8 antibodies (at a 1:500 dilution) detected a protein of approximately the predicted molecular weight for the mature C-terminal fragment of GDF-8 in the conditioned media of cells transfected with a construct in which GDF-8 had been cloned in the correct (sense) orientation with respect to the metallothionein promoter (lane 2); this band was not detected in a similar sample prepared from cells transfected with a control antisense construct (lane 1). Similar results were obtained using antibodies prepared in chickens. Hence, GDF-8 is secreted and proteolytically processed by these transfected mammalian cells.

EXAMPLE 5

EXPRESSION PATTERN OF GDF-8

Figure 10A:
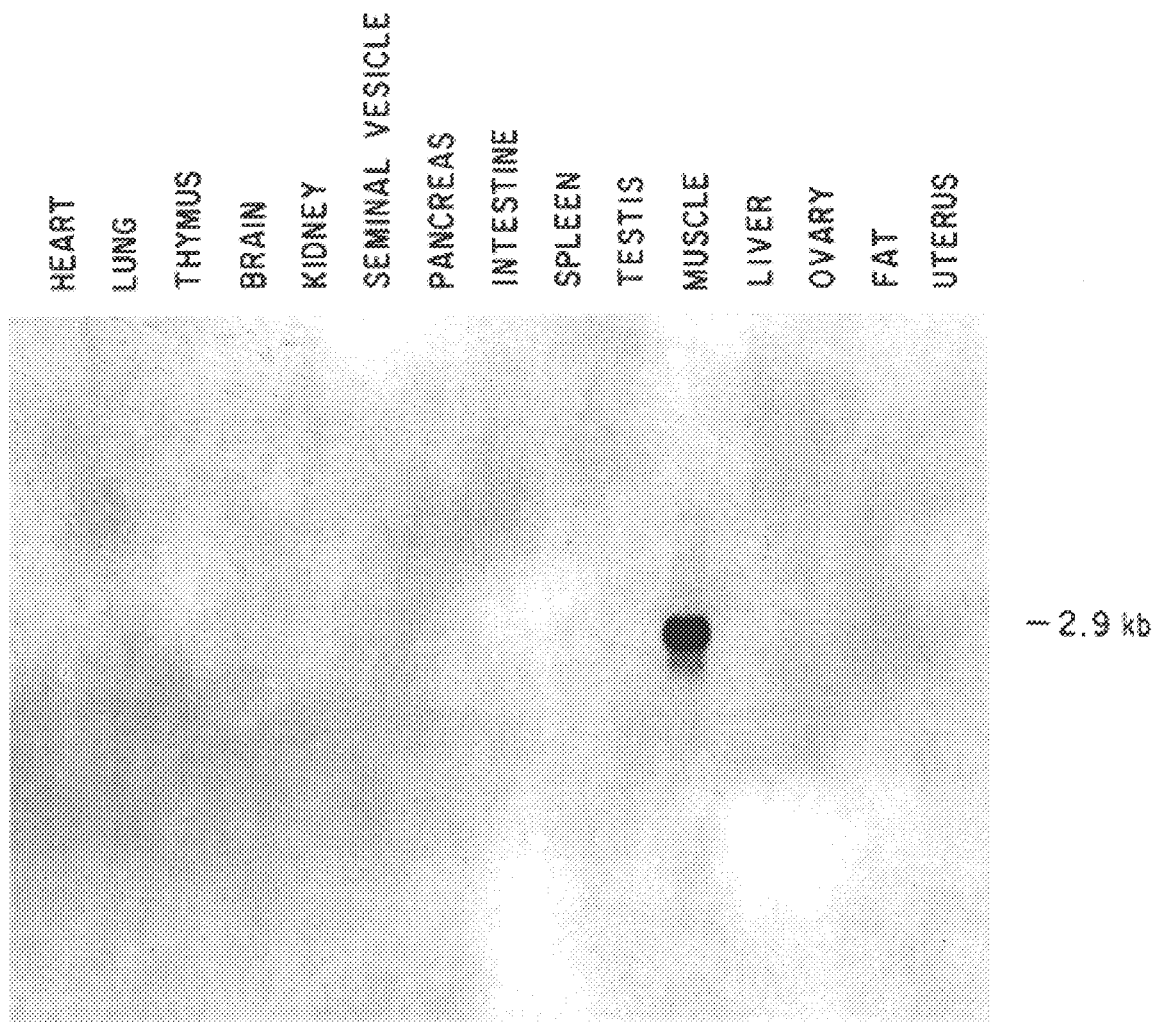
FIGS. 10(a–b) shows the expression of GDF-8 mRNA. Poly A-selected RNA (5 µg each) prepared from adult tissues (FIG. 10a) or placentas and embryos (FIG. 10b) at the indicated days of gestation was electrophoresed on formaldehyde gels, blotted, and probed with full length murine GDF-8.
Figure 10B:
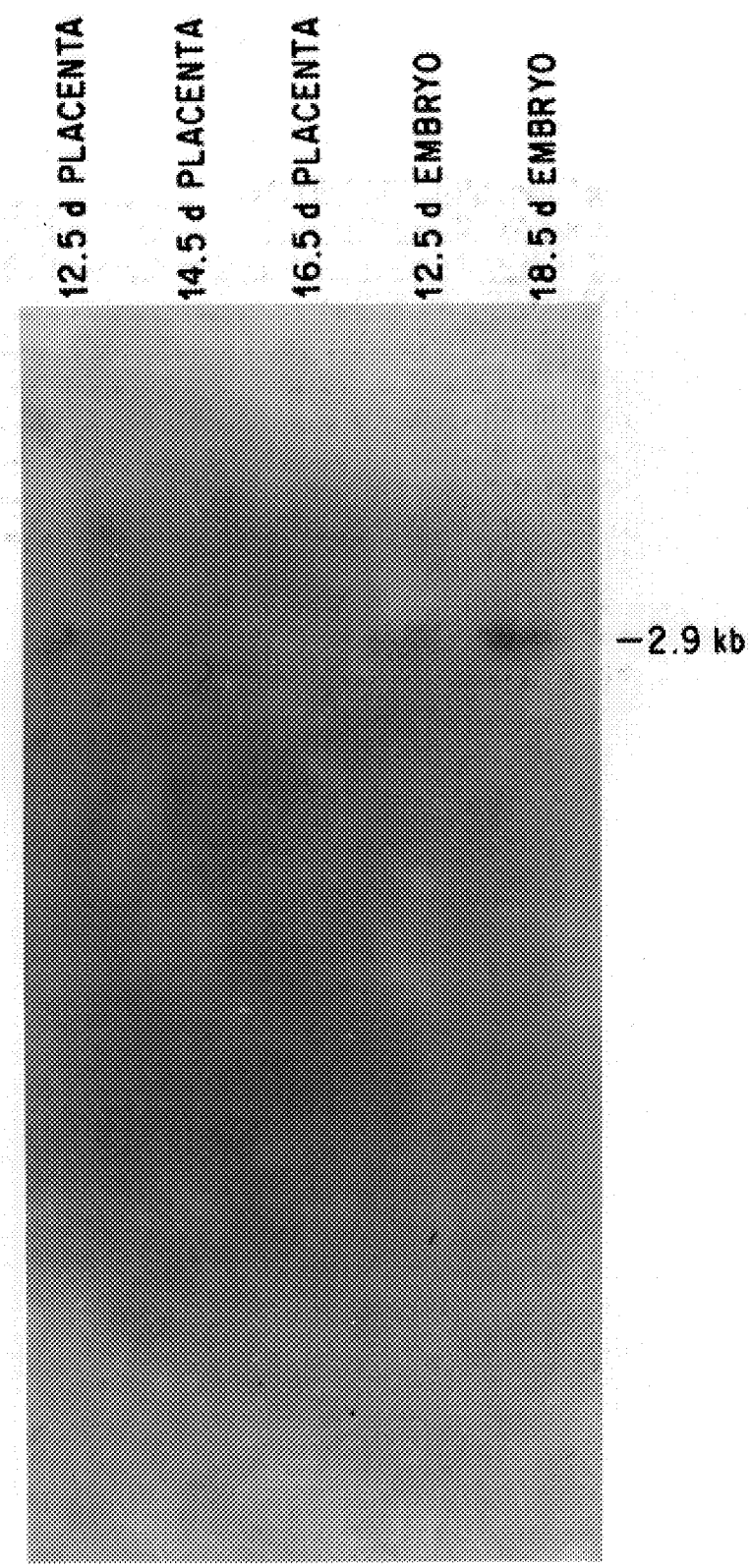

To determine the pattern of GDF-8, 5 µg of twice poly A-selected RNA prepared from a variety of murine tissue sources were subjected to Northern analysis. As shown in FIG. 10a (and as shown previously in Example 2), the GDF-8 probe detected a single mRNA species present almost exclusively in skeletal muscle among a large number of adult tissues surveyed. On longer exposures of the same blot, significant lower but detectable levels of GDF-8 mRNA were seen in fat, brain, thymus, heart, and lung. Hence, these results confirm the high degree of specificity of GDF-8 expression in skeletal muscle. GDF-8 mRNA was also detected in mouse embryos at both gestational ages (day 12.5 and day 18.5 post-coital) examined but not in placentas at various stages of development (FIG. 10b).

EXAMPLE 6

CHROMOSOMAL LOCALIZATION OF GDF-8

In order to map the chromosomal location of GDF-8, DNA samples from human/rodent somatic cell hybrids (Drwinga, et al., Genomics, 16:311–413, 1993; Dubois and Naylor, Genomics, 16:315–319, 1993) were analyzed by polymerase chain reaction followed by Southern blotting. Polymerase chain reaction was carried out using primer #83, 5'-CGCGGATCCGTGGATCTAAATGAGAACAGTGA-GC-3'(SEQ ID NO:15) and primer #84, 5'-CGCGAATTCTCAGGTAATGATTGTTTCCGTTGT-AGCG-3'(SEQ ID NO:16) for 40 cycles at 94° C. for 2 minutes, 60° C. for 1 minute, and 72° C. for 2 minutes. These primers correspond to nucleotides 119 to 143 (flanked by a Bam H1 recognition sequence), and nucleotides 394 to 418 (flanked by an Eco R1 recognition sequence), respectively, in the human GDF-8 cDNA sequence. PCR products were electrophoresed on agarose gels, blotted, and probed with oligonucleotide #100, 5'-ACACTAAATCTTCAAGAATA-3'(SEQ ID NO:17), which corresponds to a sequence internal to the region flanked by primer #83 and #84. Filters were hybridized in 6×SSC, 1×Denhardt's solution, 100, µg/ml yeast transfer RNA, and 0.05% sodium pyrophosphate at 50° C.

Figure 11:
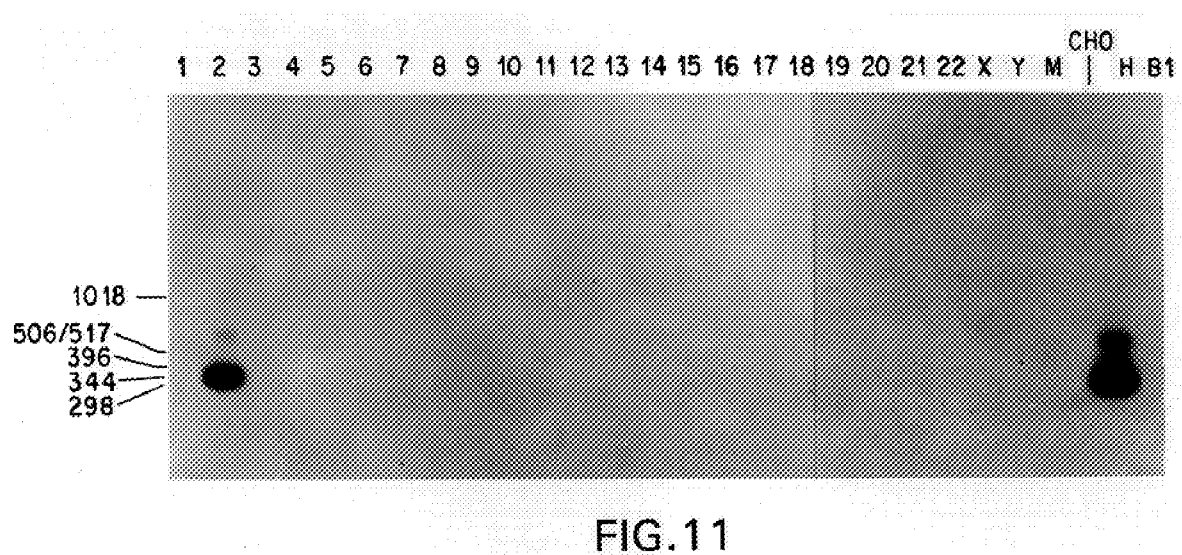
FIG. 11 shows chromosomal mapping of human GDF-8. DNA samples prepared from human/rodent somatic cell hybrid lines were subjected to PCR, electrophoresed on agarose gels, blotted, and probed. The human chromosome contained in each of the hybrid cell lines is identified at the top of each of the first 24 lanes (1-22, X, and Y). In the lanes designated M, CHO, and H, the starting DNA template was total genomic DNA from mouse, hamster, and human sources, respectively. In the lane marked B1, no template DNA was used. Numbers at left indicate the mobilities of DNA standards.

As shown in FIG. 11, the human-specific probe detected a band of the predicted size (approximately 320 base pairs) in the positive control sample (total human genomic DNA) and in a single DNA sample from the human/rodent hybrid panel. This positive signal corresponds to human chromosome 2. The human chromosome contained in each of the hybrid cell lines is identified at the top of each of the first 24 lanes (1–22, X, and Y). In the lanes designated M, CHO, and H, the starting DNA template was total genomic DNA from mouse, hamster, and human sources, respectively. In the lane marked B1, no template DNA was used. Numbers at left indicate the mobilities of DNA standards. These data show that the human GDF-8 gene is located on chromosome 2.

Although the invention has been described with reference to the presently preferred embodiment, it should be understood that various modifications can be made without departing from the spirit of the invention. Accordingly, the invention is limited only by the following claims.

SUMMARY OF SEQUENCES

SEQ ID NO:1 is the nucleic acid sequence for clone SJL141.
SEQ ID NO:2 is the nucleic acid sequence for clone SJL147.
SEQ ID NO:3 is the nucleic acid sequence for clone ACM13.
SEQ ID NO:4 is the nucleic acid sequence for clone ACM14.
SEQ ID NO:5 is the partial nucleotide sequence and deduced amino acid sequence for murine GDF-8.
SEQ ID NO:6 is the deduced partial amino acid sequence for murine GDF-8.
SEQ ID NO:7 is the partial nucleotide sequence and deduced amino acid sequence for human GDF-8.
SEQ ID NO:8 is the deduced partial amino acid sequence for human GDF-8.
SEQ ID NO:9 is the amino acid sequence for primer SJL141.
SEQ ID NO:10 is the amino acid sequence for primer SJL147.
SEQ ID NO:11 is the nucleotide and deduced amino acid sequence for murine GDF-8.
SEQ ID NO:12 is the deduced amino acid sequence for murine GDF-8.
SEQ ID NO:13 is the nucleotide and deduced amino acid sequence for human GDF-8.
SEQ ID NO:14 is the deduced amino acid sequence for human GDF-8.
SEQ ID NO's:15 and 16 are nucleotide sequences for primer #83 and #84, respectively, which were used to map human GDF-8 in human/rodent somatic cell hybrids.
SEQ ID NO:17 is the nucleotide sequence of oligonucleotide #100 which corresponds to a sequence internal to the region flanked by primer #83 and #84.

We claim:

1. Substantially pure growth differentiation factor-8 (GDF-8) having the amino acid sequence as set forth in SEQ ID NO:12 or SEQ ID NO:14.

2. An isolated polynucleotide encoding the GDF-8 polypeptide having the amino acid sequence as set forth in SEQ ID NO:12 or SEQ ID NO:14.

3. An isolated polynucleotide selected from the group consisting of:

a) SEQ ID NO:11;

b) SEQ ID NO:13;

c) SEQ ID NO:11, wherein T can also be U;

d) SEQ ID NO:13, wherein T can also be U;

e) nucleic sequences complementary to SEQ ID NO:11;

f) nucleic sequences complementary to SEQ ID NO:13;

g) fragments of a) c), or e) that are at least 15 bases in length and that will selectively hybridize to genomic DNA which encodes the GDF-8 protein of SEQ ID NO:12; and h) fragments of b), d), or f) That are at least 15 bases in length and that will selectively hybridize to genomic DNA which encodes the GDF-8 protein of SEQ ID NO:14.

4. The polynucleotide of claim 2, wherein the polynucleotide is isolated from a mammalian cell.

5. The polynucleotide of claim 4, wherein the mammalian cell is selected from the group consisting of mouse, rat, and human cell.

6. An expression vector including the polynucleotide of claim 2.

7. The vector of claim 6, wherein the vector is a plasmid.

8. The vector of claim 6, wherein the vector is a viral vector.

9. A host cell containing the vector of claim 6.

10. The host cell of claim 9, wherein the cell is prokaryotic.

11. The host cell of claim 9, wherein the cell is eukaryotic.

* * * * *